United States Patent [19] [11] 4,159,386
Kienzle et al. [45] Jun. 26, 1979

[54] SYNTHESIS OF CYCLOPENTANOL

[75] Inventors: Frank Kienzle, Therwil, Switzerland; Perry Rosen, North Caldwell, N.J.

[73] Assignee: Hoffmann-La Roche Inc., Nutley, N.J.

[21] Appl. No.: 880,835

[22] Filed: Feb. 24, 1978

Related U.S. Application Data

[60] Division of Ser. No. 613,652, Sep. 15, 1975, Pat. No. 4,089,889, which is a division of Ser. No. 381,322, Jul. 20, 1973, abandoned, and a continuation-in-part of Ser. No. 300,633, Nov. 25, 1972, abandoned.

[51] Int. Cl.$^2$ ............................................. C07C 69/74
[52] U.S. Cl. ................................. 560/126; 260/586 R
[58] Field of Search ..................... 260/586 R; 560/126

[56] References Cited

FOREIGN PATENT DOCUMENTS 36690 2/1968 Finland ................................. 260/586 R
556811 12/1974 Switzerland ........................ 260/586 R

OTHER PUBLICATIONS

Mukharji, P. K. et al., Tetrahedron, vol. 25, pp. 5287–5294, 1969.

Primary Examiner—Paul J. Killos
Attorney, Agent, or Firm—Jon S. Saxe; Bernard S. Leon; William H. Epstein

[57] ABSTRACT

Process for synthesizing the lactone, (dl) 3,3a beta-4,5-6,6a beta-hexahydro-4beta(3-hydroxyl-1-trans-octenyl)-5alpha-hydroxy-2-oxo-2H-cyclopenta[b]furan, a known intermediate for producing prostaglandin $E_2$ and $F_{2\alpha}$ and a process for preparing 11-desoxy and 11-alkyl prostaglandins from dihydroresorcyclic acid.

2 Claims, No Drawings

SYNTHESIS OF CYCLOPENTANOL

CROSS REFERENCE TO RELATED APPLICATIONS

This is a division of application Ser. No. 613,652 filed Sept. 15, 1975, now U.S. Pat. No. 4,089,889 which in turn is a divisional of Ser. No. 381,322 filed July 20, 1973 and a continuation-in-part of 300,633, filed Nov. 25, 1972, both abandoned.

BACKGROUND OF THE INVENTION

Prostagladins are well known therapeutic agents. For example, prostaglandin $F_{2\alpha}$ and $E_2$ are known agents for inducing labor in pregnant women and for the therapeutic termination of pregnancy.

In an article by Corey et al. entitled "Stereo Controlled Synthesis of Prostaglandin $F_{2\alpha}$ and $E_2$ (dl)," *Journal of American Chemical Society*, Vol., 91, pp. 5675–5678 (1969), there is disclosed the synthesis of various prostaglandins such as $E_2$ and $F_{2\alpha}$ from (dl) 3,3a beta-4,5,6,6a beta-hexahydro-4 beta (3-hydroxy-1-trans-octenyl)-5 alpha-hydroxy-2-oxo-2H-cyclopenta[b] furan, which has the formula:

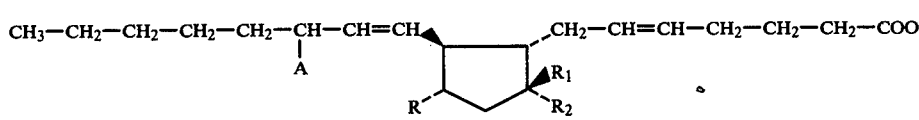

SUMMARY OF THE INVENTION

In accordance with this invention, a process is provided for synthesizing prostaglandins of the formula:

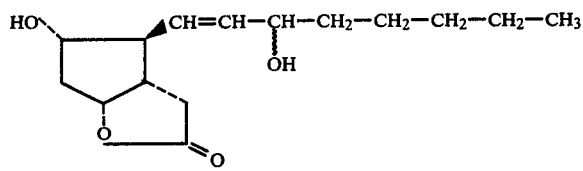

wherein A is ---OH, ⁓OH, or ◢OH; R is hydrogen, hydroxy and lower alkyl; $R_1$ is hydrogen; $R_2$ is hydroxy, or $R_1$ and $R_2$ taken together are oxo; and the known intermediates of formula I from a compound of the formula:

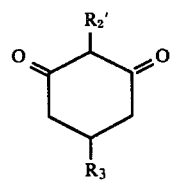

wherein $R_3$ is hydrogen, lower alkyl or carboxy; and $R_2'$ is carboxymethyl or a potential carboxymethyl group; via an intermediate of the formula:

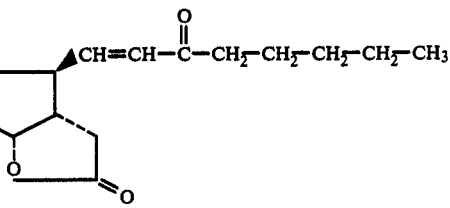

wherein $R_4$ is carboxy, a carboxy protected with a group convertible thereto by hydrolysis, hydrogen or lower alkyl.

DETAILED DESCRIPTION OF THE INVENTION

As used throughout this application, the term "lower alkyl" included both straight chain and branched chain alkyl groups having from 1 to 7 carbon atoms, such as methyl, ethyl and propyl, preferably methyl. As used herein, the term "lower alkoxy" comprehends groups having from 1 to 7 carbon atoms such as methoxy and ethoxy. As also used herein, the term "lower alkanoic acids" comprehends an alkanoic acid of 1 to 7 carbon atoms such as formic acid and acetic acid. As further used herein, the term "halogen" or "halo", unless otherwise stated, comprehends fluorine, chlorine, bromine and iodine.

In the process of this invention, all compounds having one or more asymmetric carbon atoms can be produced as racemic mixtures. These racemic mixtures which are obtained can be resolved at the appropriate steps in the process of this invention by methods well known in the art discussed more fully below, whereupon subsequent products may be obtained as the corresponding optically pure enantiomers.

In the pictorial representation of the compounds given throughout this application, a thickened tapered line (◣) indicates a substituent which is in the β-orientation (above the plane of the molecule), a dotted line (---) indicates a substituent which is in the α-orientation (below the plane of the molecule) and a wavy line (⁓) indicates a substituent which is in either the α- or β-orientation. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aryl lower alkanoic acid" comprehends acids wherein "aryl" and "lower alkanoic acid" are as defined above, particularly benzoic acid.

As still further used herein, the term "carboxy protected with a group convertible thereto by hydrolysis" comprehends any conventional organic acid protecting group which can be removed by hydrolysis. The preferred organic acid protecting groups are the esters. Any conventional ester that can be hydrolyzed to yield the acid can be utilized as the protecting group. Exemplary esters useful for this purpose are the lower alkyl esters, particularly methyl and ethyl ester, the aryl esters, particularly phenyl ester and the aryl lower alkyl esters, particularly benzyl ester.

As used herein, the term "hydrolyzable ester or ether group" designates any ester or ether which can be hydrolyzed to yield the hydroxy group. Exemplary ester groups useful for this purpose are those in which the acyl moiety is derived from a lower alkanoic, an aryl lower alkanoic, phosphoric, carbonic or a lower alkane dicarboxylic acid. Among the acids which can be utilized to form such ester groups are the acid anhydrides and the acid halides, preferably chlorides or bromides, with the lower alkanoic acid anhydrides, e.g., acetic anhydride and caproic anhydride, the aryl lower alkanoic acid anhydrides, e.g., benzoic acid anhydrides, lower alkane dicarboxylic acid anhydrides, e.g., succinic anhydride, and chloroformates, e.g., trichloroethylchloroformate, being preferred. A suitable ether protecting group is, for example, the tetrahydropyranyl ether or 4-methoxy-5,6-dihydro-2H-pyranyl ether. Others are arylmethyl ethers such as benzyl, benzhydryl, or trityl ethers or α-lower alkoxy lower alkyl ether, for example, methoxymethyl or allylic ethers, or alkyl silyl ethers such as trimethyl silyl ether.

As still further used throughout this application, the term "potential carboxymethyl group" comprehends a group which can be converted to carboxymethyl. In accordance with this invention, any conventional group convertible to carboxymethyl can be utilized. Among the preferred potential carboxymethyl groups are the groups which can be converted or hydrolyzed to a carboxymethyl group. Exemplary potential carboxymethyl groups are the groups:

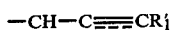  (A)

wherein $R_1'$ is hydrogen or lower alkyl and the dotted bond can be an additional unsaturated bond; such as 2-propynyl and 2-butynyl and the groups:

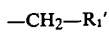  (B)

wherein R' is a conventional group convertible to a carboxy group by hydrolysis; such as methoxycarbonylmethyl and benzyloxycarbonylmethyl. The particularly preferred potential carboxymethyl group is 2-propenyl.

The compound of formula II includes prostaglandins $E_2$ and $F_{2\alpha}$ as well as other known prostaglandins, all of which are useful in the same manner as prostaglandin $F_{2\alpha}$ as an agent for inducing labor in pregnant women and for the therapeutic termination of pregnancy.

The compound of formula III is formed from alpha-dihydroresorcyclic acid or a compound of the formula:

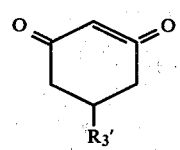  III-A wherein $R_3'$ is hydrogen or lower alkyl; by treating dihydroresorcyclic acid or the compound of formula IV with alpha-chloro acetic acid or a potential carboxymethyl halide of the formula:

  XVIII wherein $R_2'$ is as above; $X_1$ is chlorine, bromine or iodine, preferably bromine.

Preferably a potential carboxymethyl halide is utilized, of the formula:

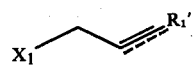  XVIII-A wherein $X_1$ and $R_1'$ are as above; and the dotted bond can be an additional unsaturated bond.

The reaction of dihydroresorcyclic acid or the compound of formula II-A with the halide of formula XVIII can be carried out in an aqueous medium containing an alkali metal hydroxide and in the presence of a powdered copper catalyst. In carrying out this reaction, any conventional alkali metal hydroxide can be utilized, with potassium hydroxide being preferred. In this reaction the alkali metal hydroxide can be present in an amount of from about 10 and 30% by weight of the aqueous medium. In carrying out this reaction, temperature and pressure are not critical, and in general, the reaction can be carried out at room temperature (22° C.) and atmospheric pressure. Preferably, the reaction is carried out at a temperature of from about −10° C. to about 65° C., under an inert gas atmosphere. In carrying out this reaction, any conventional inert gas such as nitrogen or argon may be utilized, and it is particularly preferred to bubble the inert gas through the reaction mixture while, at the same time, vigorously stirring the reaction mixture.

In accordance with the process of this invention, the compound of formula IV can be prepared from the compound of formula III via the following reaction scheme:

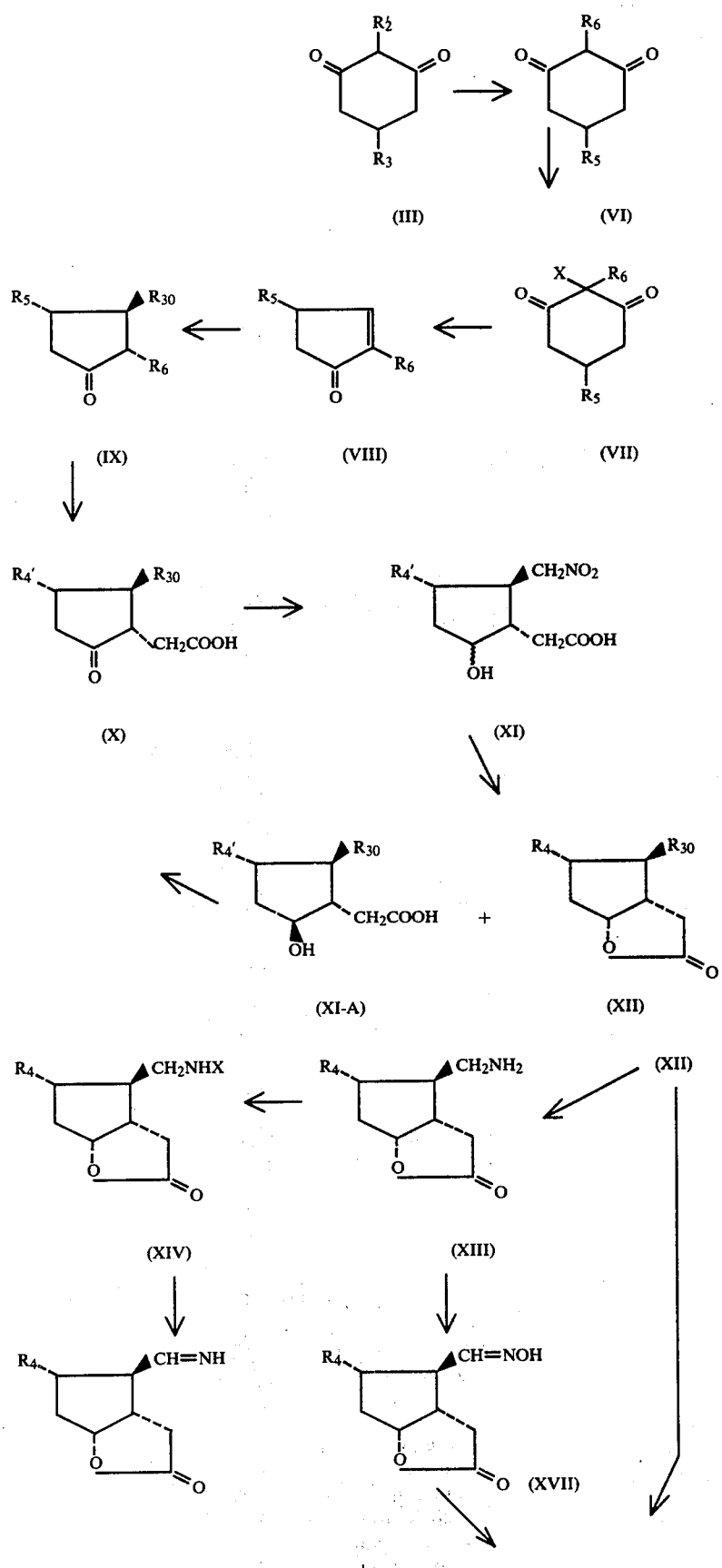

(XV)

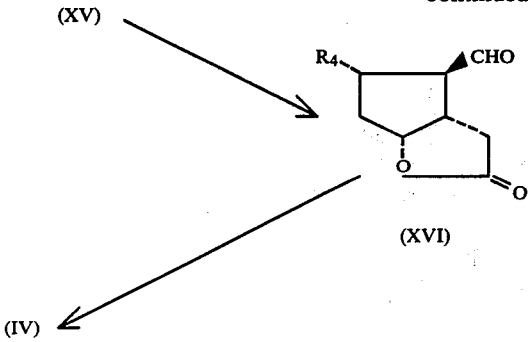

(XVI)

(IV)

wherein $R_3$, $R_4$ and $R_2'$ are as above; $R_6$ is a potential carboxymethyl group; $R_4'$ is hydrogen, lower alkyl or carboxy; $R_5$ is hydrogen, lower alkyl and a conventional group convertible to carboxy by hydrolysis; X is chlorine or bromine; preferably chlorine; $R_{30}$ is —CH$_2$NO$_2$ or —C≡N.

In accordance with the process of this invention, the carboxy substituent or substituents on the compound of formula III can be protected by esterification. In obtaining the compound of formula VI, where $R_5$ and $R_6$ is a protected carboxy group, the compound of formula III can be esterified by any conventional means. In carrying out the protection of the carboxy group, it is preferred to react the compound of formula III with a lower alkanol or benzyl alcohol. This reaction can be carried out by conventional esterification methods utilizing conventional inert organic solvents such as a lower alkanol, a lower alkyl ether, acetone, tetrahydrofuran, dioxane, diglyme, or an aliphatic or aromatic hydrocarbon. In general, the reaction is preferably carried out in an excess of the alcohol reagent. This reaction is preferably carried out in the presence of a catalytic amount of a mineral acid. Any conventional mineral acid may be utilized, with sulfuric acid being preferred. In carrying out this reaction, temperature and pressure are not critical, and in general, the reaction can be carried out at room temperature and atmospheric pressure. However, it is generally preferred to utilize temperatures of about 50° C. to about 150° C., with the reflux temperature of the reaction mixture being preferred.

It should be particularly noted that where $R_2'$ in the compound of formula III is carboxymethyl, esterification of the compound of formula III, where $R_3$ is carboxy, also esterifies the carboxymethyl substituent as well as the carboxy substituent defined by $R_3$. Hence, esterification of the compound of formula III converts each carboxy substituent thereon to a carboxy protecting group removable by hydrolysis.

The compound of formula VII can be obtained by chlorinating or brominating the compound of formula VI. In carrying out this reaction, any conventional chlorinating or brominating agent can be utilized. Among the preferred chlorinating agents are chlorine dissolved in a chlorinated hydrocarbon, tert-butylhypochlorite, and N-chlorosuccinimide, particularly tert-butylhypochlorite. Among the preferred brominating agents are included bromine dissolved in a halogenated hydrocarbon or n-bromo-succinimide or acetamide. This reaction can be carried out in an inert organic solvent. In carrying out this reaction, any conventional, inert organic solvent can be utilized, such as the halogenated hydrocarbons, the lower alkanols, diethyl ether and tetrahydrofuran. In utilizing tert-butylhypochlorite, the lower alkanols, particularly methanol, are the preferred solvents. In carrying out this reaction, temperature and pressure are not critical, and in general, the reaction can be carried out at room temperature and atmospheric pressure. In carrying out this reaction, temperatures of about −10° C. to about 100° C. are generally utilized with temperatures of from 0° C. to 20° C. being particularly preferred.

The cyclopentenyl compound of formula VIII can be obtained by the ring contraction of the compound of formula VII. In carrying out this ring contraction, the compound of formula VII is preferably heated to an elevated temperature in the presence of a non-hydroxyl base. In carrying out this reaction, any conventional non-hydroxyl base can be utilized. In general, the anhydrous alkali metal carbonates, sodium bis-trimethyl silylamide, lithium diisopropylamide and powdered glass are the preferred non-hydroxyl bases, particularly anhydrous sodium carbonate. This reaction can be carried out in an inert organic, high-boiling solvent, preferably under an inert gas atmosphere such as nitrogen or argon. In carrying out this reaction, any conventional inert organic high-boiling solvent can be utilized with the aromatic hydrocarbons, being preferred, particularly xylene and mesitylene. In carrying out this reaction, an elevated temperature of about 100° C. to about 200° C. can be utilized. In general, it is preferred to carry out this reaction at the reflux temperature of the reaction mixture, with a temperature of about 140° C. to about 170° C. being particularly preferred.

The compound of formula IX where $R_{30}$ is —CH$_2$NO$_2$ can be obtained by treating the compound of formula VIII with nitromethane in the presence of a base. In carrying out this reaction, any conventional base may be utilized. Among the preferred bases are the lower alkoxides, particularly the alkali metal lower alkoxides, and the amines, particularly the tertiary and quaternary amines, and pyridine. Particularly preferred as the base is benzyltrimethyl-ammonium hydroxide. This reaction can be carried out in an inert organic solvent. In this reaction, any conventional, inert organic solvent can be utilized, such as a lower alkanol, a lower alkyl ether, tetrahydrofuran, dioxane or diglyme. In carrying out this reaction, it is preferred to utilize an excess of nitromethane as the solvent. In carrying out this reaction, temperature and pressure are not critical, and in general, the reaction can be carried out at room temperature and atmospheric pressure. In carrying out this reaction, it is preferred to utilize a temperature of about −30° C. to the reflux temperature of the reaction mixture with a temperature of about 100° C. being particularly preferred.

The compound of formula IX where $R_{30}$ is $-C\equiv N$ can be prepared by reacting the compound of formula IX with a cyanolating agent. Any conventional cyanolating agent can be utilized. Among the preferred cyanolating agents are dilower alkyl aluminum cyanide, and the cyanohydrin of acetone. Where a cyanohydrin of acetone is utilized, the reaction is carried out in the presence of an alkali metal carbonate in an aqueous alcoholic medium such as aqueous ethanol. Where a dialkyl aluminum cyanide is utilized, the reaction is carried out in an inert organic solvent such as toluene or benzene. In carrying out this reaction, temperature and pressure are not critical and this reaction can be carried out at room temperature or atmospheric pressure. If desired, higher or lower temperatures can be utilized. Generally, temperatures of from 0° to 50° C. are preferred.

In the formation of the compound of formula IX from the compound of formula VIII, the substituents $R_5$ and $R_6$ have the same planer orientation about the cyclopentyl radical, i.e., either both above or both below the plane of the cyclopentyl radical. On the other hand, the nitromethane substituent is attached to the molecule on the opposite side of the plane as the substituents $R_5$ and $R_6$. This orientation is carried out throughout the rest of the process whereby a compound of formula IX is converted to a compound of formulae I or II.

The compound of formula X is obtained from the compound of formula IX by converting the potential carboxymethyl group to a carboxymethyl group. This conversion can be carried out in a conventional manner, such as by the oxidative degradation of the compound of formula IX wherein $R_6$ is

$R_1'$ and $R_1'$ is as above, or by the hydrolysis of the compound of formula IX wherein $R_6$ is $-CH_2-R'$ and $R'$ is as above.

In carrying out the oxidative degradation of the compound of formula IX, any conventional oxidizing agent which will selectively oxidize a 2-propynyl or 2-propenyl group to form a carboxymethyl group can be utilized. In general, the alkali metal permanganates, osmium tertoxide/periodate, and ozone are the preferred oxidizing agents, with potassium permanganate being particularly preferred. This oxidative degradation can be carried out in an inert solvent. In carrying out this reaction, any conventional inert solvent can be utilized, such as water and the organic solvents mentioned hereinbefore, with acetone being preferred. In carrying out this reaction, temperature and pressure are not critical, and in general, a temperature of about −70° C. to the reflux temperature of the reaction mixture can be utilized with about −40° C. to about +20° C. being particularly preferred and about 0° C. being quite particularly preferred.

In carrying out the hydrolysis of the compound of formula IX, any conventional method of hydrolysis can be utilized. Generally, it is preferred to utilize a dilute aqueous mineral acid, such as sulfuric acid or an aqueous alkali such as sodium hydroxide.

It should be noted that as a result of the hydrolysis of the compound of formula IX, each substituent which is a conventional group convertible to a carboxy group by hydrolysis, is converted to a free carboxy substituent. For this reason, it is preferred that the potential carboxymethyl substituent be a group of formula XVIII-A.

If desired, the acid of formula X is converted to its optically active isomeric form by any conventional means of resolving an acid. In carrying out the optical resolution, any conventional basic optically active resolving agent can be reacted with the acid of formula X to resolve the optical enantiomers. The preferred basic resolving agents are the amines, particularly α-phenethylamine. In carrying out this reaction, either enantiomer of the basic, optically active compound can be utilized to separate the d,l-carboxy compound of formula X. This resolution can be carried out in an inert organic solvent. In this reaction, any conventional inert organic solvent can be utilized, such as the solvents mentioned hereinbefore, preferably tetrahydrofuran. In this reaction, temperature and pressure are not critical, and the reaction can be carried out at room temperature and atmospheric pressure. If desired, either optically active enantiomers of formula X can be converted by the process of this invention to a desired optically active form of the compound of formula X. On the other hand, a racemate of the compound of formula X can be converted by the process of this invention to the racemate of formula I.

The compound of formula XI can be obtained by the selective reduction of the compound of formula X. In carrying out this reaction, the compound of formula X can be treated with a reducing agent. In general, it is preferred to convert the compound of formula X to the corresponding alkali metal carboxylate before reduction thereof.

The conversion of the compound of formula X to its alkali metal carboxylate can be suitably carried out by treating the compound of formula X with an alkali metal lower alkoxide, with sodium methoxide being preferred. In carrying out this reaction, conventional methods of converting a carboxylic acid or dicarboxylic acid to an alkali metal salt thereof can be utilized.

In carrying out the selective reduction of the compound of formula X to give the compound of formula XI, any conventional reducing agent which will selectively reduce the 4-keto group to a 4-hydroxy group without affecting a carboxyl group can be utilized. In general, a hydride reducing agent is preferred, such as an alkali metal hydride or borohydride. A particularly preferred reducing agent is lithium perhydro-9b-boraphenalylhydride. In carrying out this reaction, temperature and pressure are not critical, and the reaction can be carried out at room temperature and atmospheric pressure. In general, the reaction is preferably carried out at a temperature of from about −100° C. to the reflux temperature of the reaction mixture, with less than about 0° C. being the particularly preferred temperature and about −78° C. being quite particularly preferred. This reaction can be carried out in the presence of an inert organic solvent. In carrying out this reaction, any conventional inert organic solvent, such as the solvents mentioned hereinbefore, can be utilized.

The compound of formula XI can be converted to the compound of formula XII by heating the compound of formula XI in an inert organic solvent. In carrying out this conversion, temperature and pressure are not critical and, in general, the reaction can be carried out at a temperature of from about 50° C. to about 100° C. and at atmospheric pressure, with the reflux temperature being preferred. This reaction can be carried out in a conventional inert organic solvent such as the solvents mentioned hereinbefore, preferably tetrahydrofuran.

In carrying out the lactonizing procedure, only the isomer of formula XI where the hydroxy group is on the same side of the plane of the molecule as the carboxymethyl substituent, lactonizes to form the compound of formula XII. Hence, in the conversion of the compound of formula XI to the compound of formula XII, the compound of formula XI-A is produced as a side product. The compound of formula XI-A can be separated from the compound of formula XII by forming the water soluble acid salt of the compound of formula XI-A. A conventional base such as an alkali metal carbonate or bicarbonate can be utilized to form the water soluble alkali metal salt of the compound of formula XI-A. After separation of the compound of formula XI-A from the compound of formula XII via its water soluble acid salt thereof, the compound of formula XI-A can be converted back to the compound of formula X by oxidation utilizing an oxidizing agent such as the Jones Reagent or chromium trioxide or potassium permanganate. Any of the conditions conventional in oxidizing with these oxidizing agents can be utilized in oxidizing the compound of formula XI-A to the compound of formula X.

The compound of formula XII where $R_{30}$ is $-CH_2NO_2$ can be directly converted to the compound of formula XVI by oxidizing the compound of formula XII with an oxidizing agent which selectively oxidizes a nitromethyl group to an aldehyde. The preferred oxidizing agents are the alkali metal permanganates, sodium permanganate being particularly preferred. In carrying out this reaction, the compound of formula XII is converted to its aci-nitro salt before treatment with the permanganate.

The compound of formula XII where $R_{30}$ is $-CH_2NO_2$ can be converted to its aci-nitro salt by treatment with an alkali metal lower alkoxide, preferably lithium methoxide. In carrying out this reaction, temperature and pressure are not critical, and in general, the reaction can be carried out at room temperature and atmospheric pressure. This reaction can be carried out in an inert organic solvent. In this reaction, any conventional inert organic solvent may be utilized, such as the solvents mentioned hereinbefore with methanol being preferred.

The oxidation of the aci-nitro salt of the compound of formula XII can be carried out in the presence of an inert organic solvent or water. In this reaction, any conventional inert organic solvent may be utilized such as tetrahydrofuran, dioxane, acetone, diglyme or a lower alkyl ether. In carrying out this reaction, temperature and pressure are not critical and the reaction can be carried out at room temperature and atmospheric pressure. In general, it is preferred to carry out this reaction at a temperature of about $-10°$ C. to about $+75°$ C. with a temperature of about 0° C. being particularly preferred.

Alternatively, the compound of formula XII can be converted to the compound of formula XVI via intermediates XIII, XIV, XV and XVII. In this procedure, the compound of formula XII is first hydrogenated to form the compound of formula XIII. This hydrogenation is carried out in the presence of a hydrogenation catalyst.

Before hydrogenation and before conversion to its aci-nitro salt, the compound of formula XII, wherein $R_4$ is carboxy, is preferably first protected by a conventional protecting group convertible to a carboxy group by hydrolysis. The conversion of $R_4$ from carboxy to a group convertible to carboxy can be carried out in a conventional manner by esterification, preferably in accordance with the esterification of the compound of formula III above. In the hydrogenation of the compound of formula XII, any conventional hydrogenation catalyst can be utilized such as Raney-nickel, a noble metal, and aluminum amalgam. In this reaction, the use of a noble metal such as platinum or palladium is preferred. In carrying out this reaction, temperature and pressure are not critical, and in general, the reaction can be carried out at room temperature and at atmospheric pressure. Preferably, the reaction is carried out at from about 1 to about 5 atmospheres of pressure and about 0° C. to about 20° C. The hydrogenation reaction can be carried out in an inert organic solvent. In carrying out this reaction, any conventional inert organic solvent may be utilized such as the solvents hereinbefore mentioned, preferably a lower alkanol, particularly ethanol.

The compound of formula XIV can be obtained by treating the compound of formula XIII with a chlorinating or brominating agent, preferably a chlorinating agent. In carrying out this halogenation, any conventional chlorinating or brominating agent may be utilized, with tertiary butylhypochlorite being the preferred chlorinating agent. This reaction can be carried out in an inert organic solvent. In this reaction, any conventional inert organic solvent may be utilized, such as the solvents mentioned hereinbefore. In carrying out this reaction, temperature and pressure are not critical and the reaction can be carried out at room temperature and atmospheric pressure. If desired, higher or lower temperatures may be utilized. Generally, this reaction is carried out at temperatures of $-100°$ C. to 50° C. with about 0° C. to 10° C. being preferred.

The compound of formula XV can be obtained by reacting the compound of formula XIV with a lower alkoxide preferably an alkali metal lower alkoxide such as sodium methoxide. This reaction is preferably carried out in an inert organic solvent. In carrying out this reaction, any conventional inert organic solvent may be utilized, such as the solvents hereinbefore mentioned. Among the preferred solvents are the lower alkanols. In carrying out this reaction, temperature and pressure are not critical, and the reaction can be carried out at room temperature and atmospheric pressure. In this reaction, temperatures of about 0° C. to about 100° C. are generally utilized with the reflux temperature being preferred.

The compound of formula XVI can be obtained by the hydrolysis of the compound of formula XV. In carrying out this reaction, the compound of formula XV is preferably treated with a dilute acid whereby the imino moiety in the compound of formula XV is hydrolyzed to the aldehyde moiety without affecting any hydrolyzable carboxy protecting group defined by $R_4$. In carrying out this hydrolysis with a dilute acid, about 0.05 N to about 2.0 N-aqueous acid solution is preferably utilized. In carrying out this reaction, any conventional acid can be utilized, with the mineral acids being particularly preferred and sulfuric acid being quite particularly preferred. This reaction can be carried out in water or in an inert organic solvent. Any conventional inert organic solvent may be utilized in this hydrolysis reaction, with the lower alkanols being preferred. In carrying out this reaction, temperature and pressure are not critical, and the reaction can be carried out at room temperature and atmospheric pressure. Generally, this reaction is carried out at a temperature of about 0° C. to about 50° C., with 20° C. being preferred.

The compound of formula XVI can further be alternatively obtained by oxidizing the compound of formula XIII to an oxime of formula XVII, and hydrolyzing the oxime to the aldehyde of formula XVI.

In carrying out the oxidation of the compound of formula XIII any conventional oxidizing agent for converting an amine to an oxime may be utilized, such as hydrogen peroxide, an alkali metal tungstate or an alkali metal molybdate. In carrying out this reaction, temperature and pressure are not critical and the reaction can be carried out at room temperature and atmospheric pressure. In general, the reaction is preferably carried out at a temperature of about 0° C. to about 50° C. This reaction can be carried out in an inert organic solvent. In carrying out this reaction, any conventional inert organic solvent such as the solvents mentioned hereinbefore can be utilized, with tetrahydrofuran being preferred.

The hydrolysis of the oxime of formula XVII to the compound of formula XV can be carried out in the presence of a bisulfite, preferably an alkali metal bisulfite. By this hydrolysis step with a bisulfite, the oxime moiety is hydrolyzed to the aldehyde moiety without hydrolyzing the carboxy protecting group defined by $R_4$. In this reaction, temperature and pressure are not critical and the reaction can be carried out at room temperature and atmospheric pressure. In general, the reaction is preferably carried out at a temperature of about 0° C. to about 100° C. This reaction can be carried out in an inert organic solvent. In this reaction, any conventional inert organic solvent, such as the solvents mentioned hereinbefore, can be utilized with the lower alkanols being preferred.

The compound of formula IV can be obtained by treating the compound of formula XVI with either a phosphorane of the formula:

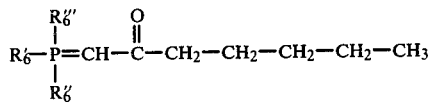

wherein $R_6'$, $R_6''$ and $R_6'''$ are aryl or di(lower alkyl)amino; or a phosphonate of the formula:

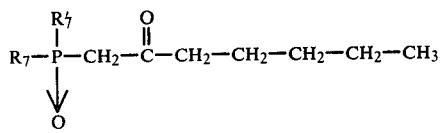

wherein $R_7$ and $R_7'$ are aryl, aryloxy or lower alkoxy.

The double bond formed in the compound of formula IV by this reaction is a trans double bond.

The reaction of a phosphorane of formula XIX with the compound of formula XVI can, if desired, be carried out utilizing conventional Wittig conditions. Any of the conditions conventional in carrying out Wittig reactions can be utilized in carrying out this reaction.

The reaction between the phosphonate of formula XX and the compound of formula XVI can be carried out by utilizing conditions conventional in Horner type reactions. Any of the conditions conventional in carrying out Horner type reactions can be utilized in carrying out this reaction.

Where $R_4$ in the compound of formula IV is a protected carboxy group, this compound can, if desired, be hydrolyzed by conventional means to form the corresponding compound of formula IV where $R_4$ is a free carboxy group.

In accordance with this invention, the compound of formula IV is next converted to a compound of the formula:

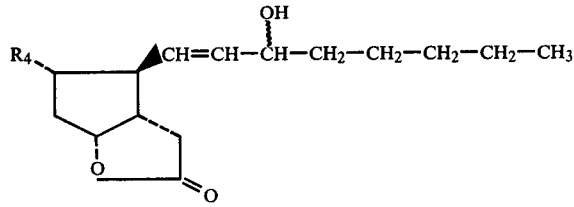

wherein $R_4$ is as above.

The compound of formula XXI can be obtained by treating the compound of formula IV with a reducing agent. In carrying out this reaction, any conventional reducing agent which will selectively reduce a keto-group to a hydroxy group can be utilized. Preferred reducing agents are the hydrides, particularly the aluminum hydrides, such as the alkali metal aluminum hydrides, and the borohydrides, such as the alkali metal borohydrides, with zinc borohydride being quite particularly preferred. In carrying out this reaction, temperature and pressure are not critical, and the reaction can be carried out at room temperature and atmospheric pressure or at elevated or reduced temperatures and pressures. Generally, it is preferred to carry out this reaction at a temperature of from −10° C. to the reflux temperature of the reaction mixture. This reduction reaction can be carried out in the presence of an inert organic solvent. Any conventional inert organic solvent or water can be utilized in carrying out this reaction, such as the conventional, inert organic solvents hereinbefore mentioned. Among the preferred solvents are dimethoxy ethylene glycol and the ethers, such as tetrahydrofuran, diethyl ether and dioxane.

The compound of formula XXI may be separated into its two isomers by conventional means to provide one isomer of the formula:

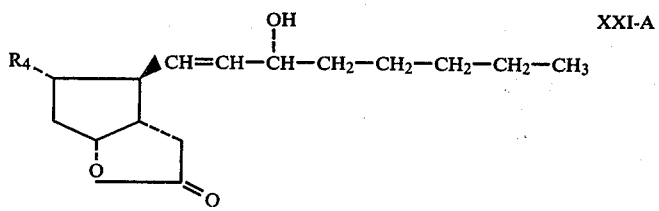

XXI-A and the other isomer of the formula:

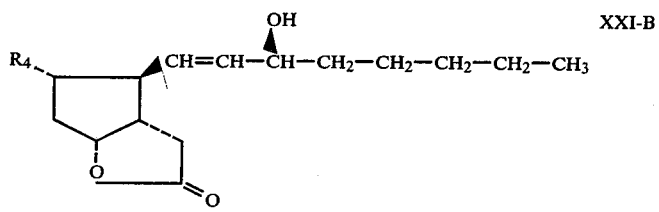

XXI-B wherein R₄ is as above.

Any conventional means of separation such as column chromatography, vapor phase chromatography, etc., can be utilized to carry out this separation.

The compound of formulae XXI, XXI-A or XXI-B can, if desired, be converted to a compound of the formula:

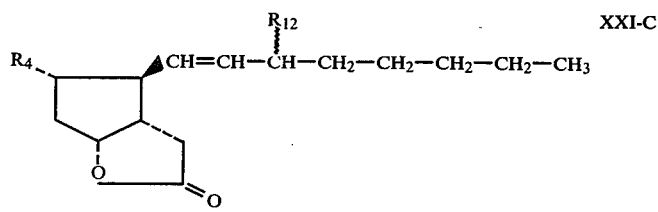

XXI-C wherein R₄ is as above; and $R_{12}$ is hydroxy or hydroxy protected with a hydrolyzable ether or ester protecting group; by esterifying or etherifying the free hydroxy group with a hydrolyzable ether or ester protecting group. This esterification or etherification can be carried out by conventional esterification or etherification procedures. Among the preferred hydrolyzable ester groups are lower alkanoyloxy with acetoxy being especially preferred. Among the preferred hydrolyzable ether groups are included tetrahydropyranyl.

In accordance with the process of this invention where R₄ is carboxy or a protected carbonyl group, either an isomer of the compound of formula XXI-C or mixtures of these isomers can be converted to the compound of formula I (Coreys Intermediate).

Where R₄ in the compound of formula XXI-C is a protected carboxy group and $R_{12}$ in the compound of XXI-C is a protected hydroxy group, the protected carboxy group R₄ can be hydrolyzed while leaving the hydroxy group $R_{12}$ protected by either an ester or ether group to produce a compound of the formula:

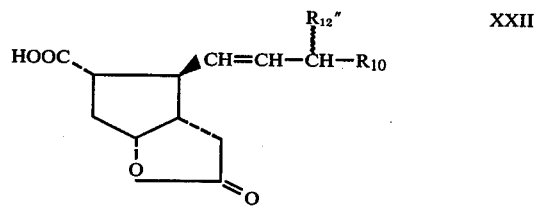

XXII wherein $R_{12}''$ is hydroxy protected with a hydrolyzable ether or ester group; and $R_{10}$ is —CH₂—CH₂—CH₂—CH₂—CH₃; via the following intermediates:

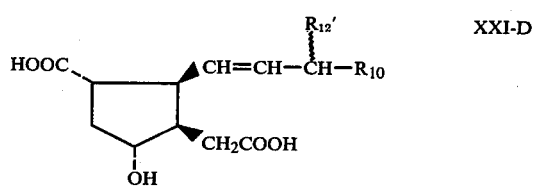

XXI-D wherein $R_{10}$ is as above; and $R_{12}'$ is hydroxy or hydroxy etherified with a hydrolyzable ether protecting group; and

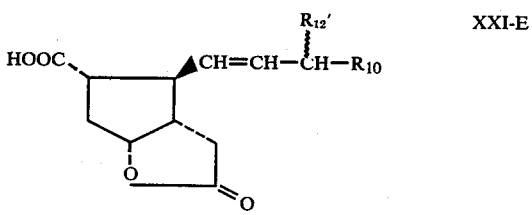

XXI-E wherein $R_{10}$, $R_4'$ and $R_{12}'$ are as above.

The compound of formula XXI-C where $R_4$ is a carboxy protecting group, is converted to the compound of formula XXI-D by hydrolysis. Any conventional method of basic hydrolysis can be utilized in this procedure. Among the preferred methods of converting the compound of formula XXI-C to the compound of formula XXI-D is by treating the compound of formula XXI-C with a dilute aqueous alkali metal hydroxide such as dilute aqueous sodium hydroxide. This basic hydrolysis will also hydrolyze $R_{12}$ where $R_{12}$ is an ester protecting group.

The compound of formula XXI-D is converted to the compound of formula XXI-E by treating the compound of formula XXI-D with a dilute aqueous mineral acid at temperatures of from 0° to 25° C. Any conventional aqueous acid can be utilized. Among the preferred acids are included dilute aqueous 0.1N to 2N-hydrohalic acids such as 0.1N-hydrochloric and 0.1N to 2N-aqueous sulfuric acid. The dilute mineral acid will not hydrolyze $R_{12}'$ where $R_{12}'$ is an ether protecting group.

The compound of formula XXIII where $R_{12}''$ is a hydrolyzable ester group is prepared from the compound of formula XXI-E where $R_{12}'$ is hydroxy by treatment with an acid esterifying agent such as a lower alkanoic acid anhydride. Any conventional method for esterifying an alcohol can be utilized in this conversion.

The compound of formula XXIII can be converted to the compound of formula I via the following intermediates:

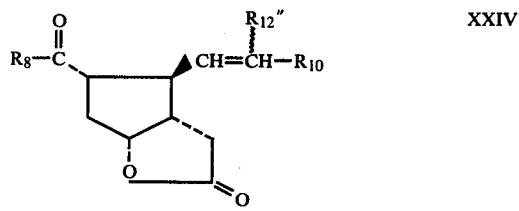

where $R_{12}''$ and $R_{10}$ are as above and $R_8$ is an activated leaving group;

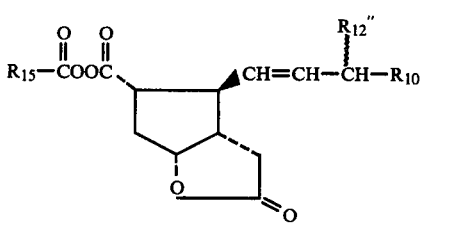

wherein $R_{10}$ and $R_{12}''$ are as above; and $R_{15}$ is the source of variation which distinguishes one per-organic acid from another.

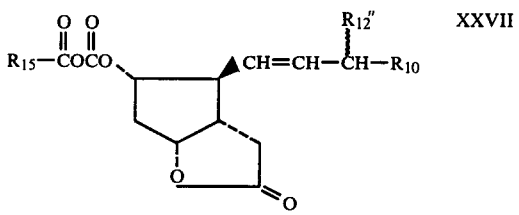

wherein $R_{10}$, $R_{15}$ and $R_{12}''$ are as above; and

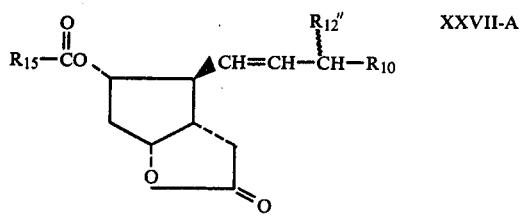

wherein $R_{10}$ $R_{15}$ and $R_{12}''$ are as above.

The compound of formula XXIII is converted to the compound of formula XXIV by treating with an agent to provide an activated leaving group on the carbonyl moiety. Any conventional activated leaving group which can be displaced from the carbonyl moiety by a peracid to promote the coupling of the peracid with the carbonyl moiety can be utilized as the substituent $R_8$. Among the preferred activated leaving groups are the chloride and bromide groups, particularly the chloride group. Any conventional method of converting a hydroxy moiety on a free carboxy acid group to an activating leaving group can be utilized. Among the compounds which react with the compound of formula XXIII to form an activating leaving group are included oxalyl chloride and thionyl chloride.

The compound of formula XXV can be obtained by treating the compound of formula XXIV with a peracid, preferably m-chloroperbenzoic acid. In this reaction, the activating leaving group $R_8$ is displaced from the carbonyl moiety by the peracid to form a mixed peranhydride of formula XXV. This reaction is preferably carried out in the presence of an organic base, such as triethylamine, collidene or pyridine, with pyridine being particularly preferred. This reaction can be carried out in an inert organic solvent. In this reaction, any conventional inert organic solvent can be utilized, such as the solvents mentioned hereinbefore. Alternatively, the reaction can be carried out in an organic base as set forth above. Preferably, the reaction is carried out in anhydrous diethyl ether. In carrying out this reaction, temperature and pressure are not critical, and the reaction can be carried out at room temperature and atmospheric pressure. In general, it is preferred to carry out the reaction at from about −20° C. to about +60° C. In carrying out this reaction, any conventional perorganic acid can be utilized such as p-nitroperbenzoic acid. The preferred perorganic acids are the aromatic perorganic acids where the aromatic group is substituted.

The compound of formula XXV can be directly produced from the compound of formula XXIII by treating the compound of formula XXIII with a perorganic acid in the presence of dicyclohexylcarbodiimide. This reaction can be carried out in an inert organic solvent such as the solvents mentioned hereinbefore. Among the preferred solvents are the ether solvents such as tetrahydrofuran, diethyl ether, etc., and the halogenated hydrocarbon solvents such as methylene chloride, etc. In carrying out this reaction, temperatures of from −20° C. to +60° C. can be utilized.

Upon refluxing the compound of formula XXV in an inert organic solvent, a mixture containing the compound of formula XXVII and XXVII-A is formed. This formation of this mixture is carried out by refluxing the compound of formula XXV in an inert organic solvent. Any conventional inert organic solvent can be utilized. Among the preferred inert organic solvents are included aromatic hydrocarbon solvents such as benzene and toluene.

The compound of formula I (Corey's Intermediate) can be obtained from the mixture of the compounds of formula XXVII and formula XXVII-A where $R_{12}''$ is a hydrolyzable ester group by basic hydrolysis. In carrying out this hydrolysis, the mixture is preferably treated with a dilute, aqueous alkali metal lower alkoxide. In this hydrolysis, any conventional alkali metal lower alkoxides can be utilized. This reaction can be carried out in the presence of an inert organic solvent. In carrying out this reaction, any conventional inert organic solvent can be utilized such as the solvents mentioned hereinbefore, preferably the ether and hydrocarbon solvent, particularly tetrahydrofuran. In carrying out this reaction, temperature and pressure are not critical, and the reaction can be carried out at room temperature and atmospheric pressure.

Basic hydrolysis of the mixture containing the compound of formula XXVII and the compound of the formula XXVII-A gives the compound of formula I. In the case where $R_{12}''$ is a hydrolyzable ester group, basic hydrolysis of the mixture directly produces Corey's Intermediate. On the other hand, where $R_{12}''$ is a hydrolyzable ether protecting group, basic hydrolysis produces the compound of formula I where the hydroxy group is protected by a hydrolyzable ether protecting group. In this case, this compound is subjected to acid hydrolysis to produce Corey's Intermediate. Any conventional method of hydrolyzing ether protecting groups can be utilized in carrying out this procedure. Dilute aqueous organic acids such as acetic acid or propionic acid can be utilized to carry out this hydrolysis.

The compound of formula I is converted to known prostaglandins by the process disclosed in the article by Corey et al. *Journal of American Chemical Society*, Vol., 91, pp. 5675–5678 (1969).

In the compounds of formulae I, XXI-C, XXI-D, XXI-E, XXIII, XXIV, XXV, XXVII and XXVII-A, the hydroxy, $R_{12}$, $R_{12}'$ and $R_{12}''$ substituents can be in either the alpha or beta orientation or these substituents may contain a mixture of these groups in the alpha and beta orientation.

Compounds of the formula XXI-C where $R_4$ is hydrogen or alkyl, i.e., compounds of the formula:

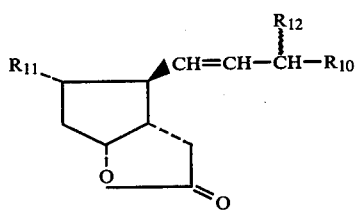

XXX wherein $R_{12}$ is as above; and $R_{11}$ is hydrogen or lower alkyl; can be converted to known prostaglandins of the formula:

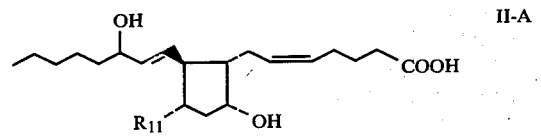

II-A wherein $R_{11}$ is as above; via the following intermediates:

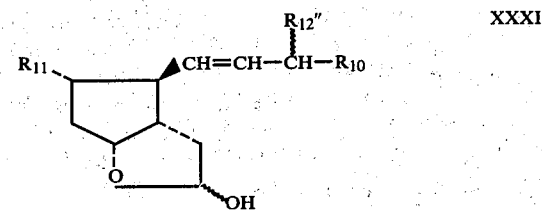

XXXI wherein $R_{10}$, $R_{11}$ and $R_{12}''$ are as above; and

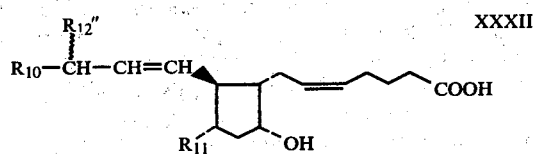

XXXII wherein $R_{10}$, $R_{11}$ and $R_{12}''$ are as above.

The free hydroxy group in the compound of formula XXX where $R_{12}$ is hydroxy can be etherified or esterified by conventional means to form the corresponding compound where $R_{12}$ is hydroxy protected with a hydrolyzable ether or ester group. This compound is converted to the compound of formula XXXI by reduction with an alkyl aluminum hydride reducing agent. Any of the conditions conventional in utilizing these reducing agents can be utilized to affect this conversion.

The compound of formula XXXI is converted to the compound of formula XXXII by reaction with a phosphorane of the formula:

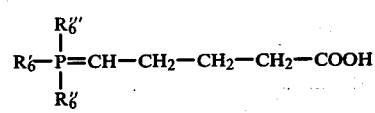

wherein $R_6'''$, $R_6'$ and $R_6''$ are as above; via a Wittig reaction. Any of the conditions standard in Wittig type reactions can be utilized in carrying out this reaction. In the Wittig reaction, the double bond formed thereby in the compound of formula XXXII is a "cis" double bond.

The compound of formula XXXII can be converted to the compound of formula II-A by conventional hydrolysis techniques utilized for hydrolyzing esters or ethers.

On the other hand, the compound of formula XXXII can be converted to a prostaglandin of formula:

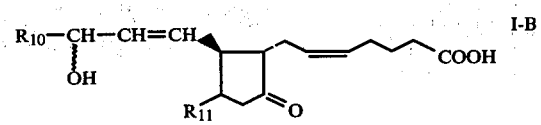

I-B wherein $R_{10}$ and $R_{11}$ are as above; via an intermediate of the formula:

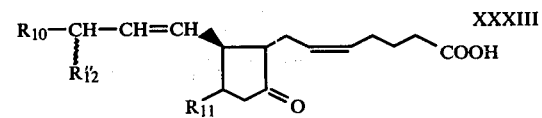

XXXIII wheren $R_{10}$, $R_{11}$ and $R_{12}''$ are as above.

The compound of formula XXXII is converted to the compound of formula XXXIII by oxidation. Any conventional oxidizing agent which will convert a hydroxy group to a keto group can be utilized in this conversion. Among the preferred oxidizing agents are chromate oxidizing agents such as chromium trioxide. Any of the conditions conventional in utilizing these oxidizing agents can be utilized in carrying out these reactions. The compound of formula XXXIII is converted to the compound of formula I-B by conventional hydrolysis procedures such as described hereinbefore.

In the compounds of the formulae II-A, I-B, XXX, XXXI, XXXII and XXXIII, the hydroxy substituent attached to the straight chain on $R_{12}''$ and $R_{12}$ can be in the alpha or beta configuration or can be mixtures of substituents in the alpha or beta configuration.

The racemic products and intermediates of this invention can be resolved into their optically active components by a number of methods of resolution well known in the art. The compounds which are acids are treated with an optically active base in the manner described hereinbefore to produce diastereoisomeric salts which can be separated by crystallization. In addition, compounds containing a free hydroxy group can be acylated with the acid chloride or anhydride of an optically active acid in the presence of an esterification catalyst, e.g., d-camphorsulfonic acid, α-bromocamphorsulfonic acid and d- and 1-6,6'-dinitrodiplenic acid to give diastereoisomeric esters which are resolvable by crystallization.

The examples which follow illustrate the invention. All temperatures are in degrees centigrade (° C.). Dilute sulfuric acid is an aqueous solution of 5% by weight sulfuric acid. Concentrated sulfuric acid is an aqueous solution of 98% by weight sulfuric acid. Dowex 50W-X8 (H+) is a polystyrene sulfonic acid-cationic ion exchange resin. A-540 (OH⁻) which is a polystyrene gel of trimethyl ammonium chloride is an anionic ion exchange resin.

EXAMPLE 1

4-(2-Propenyl)-3,5-cyclohexanedione carboxylate

To a solution of 93.6 g. of alpha-dihydroresorcyclic acid in 264 ml of 20 percent by weight aqueous potassium hydroxide was added 1.8 g of copper powder and 78 g of allyl bromide. Nitrogen was bubbled through the mixture which was stirred vigorously at room temperature for 5½ hours. 600 ml of 6 percent by weight aqueous sodium hydroxide was added and the unreacted allyl bromide removed by two extractions with 100 ml portions of diethyl ether. The basic aqueous solution was cautiously acidified with ice-cooling with 20 percent by weight aqueous sulfuric acid to pH 2. The mixture was then extracted six times with 300 ml portions of diethyl ether and dried with anhydrous magnesium sulfate. The combined, dried ether extracts were evaporated leaving a partially solid residue. Crystallization from ethyl acetate-petroleum ether gave a first crop 25.8 g, m.p. 163°–165° C. and a second crop 30.0 g. m.p. 148°–152° C., of 4-(2-propenyl)-3,5-cyclohexanedione carboxylate.

EXAMPLE 2

Methyl 4-(2-propenyl)-3,5-cyclohexanedione carboxylate 55.8 g of the 4-(2-propenyl)-cyclohexanedione carboxylate was dissolved in 700 ml of methanol, 2 g of concentrated sulfuric acid was added, and the mixture heated under reflux for 4 hours. Upon evaporation, the residue was dissolved in 200 ml of tetrahydrofuran and 100 ml of water and stirred at room temperature for 1 hour. Concentration of the mixture to half its volume, addition of 200 ml of water, five extractions with 250 ml portions of methylene chloride, gave upon evaporation of the dried (with magnesium sulfate) organic extracts crude product which after crystallization from ethyl acetate-petroleum ether afforded 38.75 g of methyl 4-(2-propenyl)-3,5-cyclohexanedione carboxylate, m.p. 130°–132° C.

EXAMPLE 3

Methyl 4-chloro-4-(2-propenyl)-3,5-cyclohexanedione carboxylate 38.75 g of methyl 4-(2-propenyl)-3,5-cyclohexanedione carboxylate was dissolved in 300 ml of tertiary-butanol and 20 g of tertiary-butyl hypochlorite in 50 ml of tertiary-butanol was added. The mixture was heated to 50° C. and stirred at that temperature for 3½ hours. Evaporation and drying in vacuo gave methyl 4-chloro-4-(2-propenyl)-3,5-cyclohexanedione carboxylate as a viscous oil. (b.p. 95°–100° C./0.01 mmHg)

EXAMPLE 4

1-Methoxycarbonyl-3(2-propenyl)-4-oxo-cyclopent-2-ene

In a three-necked flask equipped with a Dean-Stark separator, vibromixer, and a gas-inlet tube, were placed 600 ml of dry mesitylene and 75 g of anhydrous sodium carbonate. Argon was bubbled through the reaction mixture in a slow stream during the whole operation. The suspension was then heated under reflux for 2 hours before a solution of 45 g of methyl 4-chloro-4-(2-propenyl)-3,5-cyclohexanedione carboxylate in 25 ml of dry mesitylene was added dropwise during 15 min. to the boiling mixture. Refluxing and vigorous stirring was continued for 16 hours. Filtration after cooling, evaporation of the solvent and purification by distillation gave 20.15 g of 1-methoxycarbonyl-3(2-propenyl)-4-oxo-cyclopent-2-ene; b.p. 106°–111° C./0.75 mmHg.

EXAMPLE 5

4α-Methoxycarbonyl-3β-nitromethyl-2α-(2-propenyl)-cyclopentanone 20.15 g of 1-methoxycarbonyl-3(2-propenyl)-4-oxocyclopent-2-ene was dissolved in 200 ml of nitromethane and 3 ml of a 40 percent by weight methanolic solution of benzyltrimethylammoniumhydroxide was added. The mixture was then heated on a stream-bath for 3 hours, cooled and acidified with cold 2 N aqueous sulfuric acid. The mixture was then extracted with diethyl ether (300 ml). The ether solution was dried (MgSO₄) and the solvent removed under reduced pressure. Distillation of the residue afforded 4α-methoxycarbonyl-3β-nitromethyl-2α-(2-propenyl)cyclopentanone (b.p. 125°–130° C./0.15 mmHg)

EXAMPLE 6

2α-Carboxymethyl-3β-nitromethyl-4α-methoxycarbonylcyclopentanone

To an ice-cold sulution of 9.42 g of 4α-methoxycarbonyl-3β-nitromethyl-2α-(2-propenyl)cyclopentanone in 75 ml of acetone was added an ice-cold solution of 5.8 g of concentrated sulfuric acid in 75 ml of water. With cooling and vigorous stirring a solution of 21.6 g of potassium permanganate in 400 ml of water was added dropwise to the reaction mixture during 10 min. The whole operation was carried out under an atmosphere of argon. The reaction mixture was stirred for 5 min. Then, sulfur dioxide was bubbled through the mixture until a clear solution was obtained. Extraction with methylene chloride containing 20 percent by weight of acetone and evaporation of the dried (with magnesium sulfate) organic solvent afforded 4α-methoxycarbonyl-3β-nitromethyl-2α-carboxymethylcyclopentanone. The crude product was triturated with diethyl ether and filtered; m.p. 148°–150° C.

EXAMPLE 7

(−)2-Carboxymethyl-3-nitromethyl-4-methoxycarbonylcyclopentanone 518 mg of 2-carboxymethyl-3-nitromethyl-4-methoxycarbonylcyclopentanone was dissolved in 25 ml of tetrahydrofuran and 242 mg of (−)α-phenethylamine was added. Addition of a little petroleum ether and cooling gave needles of the salt of (−)α-phenethylamine and (−)2-carboxymethyl-3-nitromethyl-4-methoxycarbonylcyclopentanone which upon two recrystallizations had a constant m.p. 124°–125° C. $[\alpha]_D$ −52.46 (C.1.04, H$_2$O). Acidification with Dowex 50W-X8 (H$^+$) gave the solid, levo-rotating (−)2-carboxymethyl-3-nitromethyl-4-methoxycarbonylcyclopentanone; m.p. 111°–112° C.; $[\alpha]_D$ −79.9 (C,1.0 MeOH).

EXAMPLE 8

(+)2-Carboxymethyl-3-nitromethyl-4-methoxycarbonylcyclopentanone

Utilizing the procedure of Example 7, (+)α-phenethylamine gave the salt of (+)α-phenethylamine and (+)2-carboxymethyl-3-nitromethyl-4-methoxycarbonylcyclopentanone; m.p. 122°–123° C., $[\alpha]_D$ +58.02 (C,1.0, H$_2$O). Acidification gave the dextro-rotating(+)2-carboxymethyl-3-nitromethyl-4-methoxycarbonylcyclopentanone; m.p. 112°–113° C. $[\alpha]_D$ +84.28 (C, 1.0, MeOH).

EXAMPLE 9

3,3a beta-4,5,6,6a beta-hexahydro-4β-nitromethyl-2-oxo-2H-cyclopenta[b]furan-5α-carboxylic acid methylester To an ice-coled solution of 4.66 g. of 2α-carboxymethyl-3β-nitromethyl-4α-methoxycarbonylcyclopentanone in 250 ml. of methanol was added 0.94 g. of sodium methoxide followed by the addition of 0.5 g. of sodium borohydride. The mixture was stirred at 0° C. for 1 hour and then acidified with 1 N-aqueous sulfuric acid. Evaporation of the methanol left 2α-carboxymethyl-3β-nitromethyl-4α-methoxycarbonylcyclopentanol as a liquid residue which was extracted with a 20% by volume acetone in 80% ethyl acetate solution. The solution was dried and the solvent removed under reduced pressure. The residue was then dissolved in tetrahydrofuran and refluxed for 2 hours. The solvent was then removed and the residue treated with 15 ml. of water containing 2 g. of potassium bicarbonate. The solid was filtered to give 3,3a beta-4,5,6,6a beta-hexahydro-4β-nitromethyl-2-oxo-2H-cyclopenta[b]furan-5α-carboxylic acid methylester; m.p. 100°–101.5° C. Recrystallization from ethyl acetate petroleum ether raised the m.p. to 102°–103° C.

The bicarbonate solution was acidified and extracted with a 2:1 parts by volume solution of methylene chloride-acetone. The organic solution was dried (MgSO$_4$). The solvent was removed under reduced pressure. The residue was then crystallized from ethylacetate-petroleum ether to give 2α-carboxymethyl-3β-nitromethyl-4α-methoxycarbonyl-cyclopentane-1β-ol, m.p. 98°–100° C.

EXAMPLE 10

3,3a beta-4,5,6,6a beta-hexahydro-4β-aminomethyl-2-oxo-2H-cyclopenta[b]furan-5α-carboxylic acid methylester hydrochloride 635 mg. of 3,3a beta-4,5,6,6a beta-hexahydro-4β-nitromethyl-2-oxo-2H-cyclopenta[b]furan-5α-carboxylic acid methylester was dissolved in 100 ml. of ethanol and hydrogenated in the presence of 190 mg. of platinum oxide at room temperature in a Parr hydrogenator (53 p.s.i.) for 3½ hours. The catalyst was filtered off, the filtrate evaporated, and the free amine residue treated with ethanolic hydrogen chloride. The ethanol was removed under reduced pressure and the remaining solid suspended in an ethanol-ethyl acetate mixture and filtered giving 605 mg. of 3,3a beta-4,5,6,6a beta-hexahydro-4β-aminomethyl-2-oxo-2H-cyclopenta[b]furan-5α-carboxylic acid methylester hydrochloride; m.p. 260° C. dec. Recrystallization from aqueous methanol raised the melting point to 261° C. dec.

EXAMPLE 11

3,3a beta-4,5,6,6a beta-hexahydro-4β-carboxaldehyde-2-oxo-2H-cyclopenta[b]furan-5α-carboxylic acid methylester 243 mg. of 3,3a beta-4,5,6,6a beta-hexahydro-4-nitromethyl-2-oxo-2H-cyclopenta[b]furan-5α-carboxylic acid methylester was dissolved in 20 ml. of methanol to which 1 equivalent of lithium methoxide had been added. The clear solution, containing the acinitro salt was evaporated, the residue taken up in 5 ml. of cold water, and 2 drops of 20% by weight aqueous potassium hydroxide were added. With ice-cooling and stirring, a solution of 130 mg. of sodium permanganate trihydrate in 5 ml. of water was added dropwise over a period of 3 minutes. The reaction mixture was then quickly filtered, and the residue washed with methylene chloride. The filtrate was extracted with more methylene chloride. Evaporation of the dried (MgSO$_4$) organic solvent afforded the aldehyde 3,3a beta-4,5,6,6a beta-hexahydro-4β-carboxaldehyde-2-oxo-2H-cyclopenta[b]furan-5α-carboxylic acid methylester m.p. 94°–96°. A 2,4-dinitrophenylhydrazone of the aldehyde had a melting point of 187°–189° C.

EXAMPLE 12

3,3a beta-4,5,6,6a beta-hexahydro-4β-carboxaldehyde-2-oxo-2H-cyclopenta[b]furan-5α-carboxylic acid methylester To a suspension of 305 mg. of 3,3a beta-4,5,6,6a beta-hexahydro-4β-aminomethyl-2-oxo-2H-cyclopenta[b]furan-5α-carboxylic acid methylester hydrochloride in 25 ml. of methanol was added 5 ml. of ion exchange resin A-540(OH−), and the mixture stirred for 15 minutes. Filtration and evaporation gave 260 mg. of the free amine, i.e., 3,3a beta-4,5,6,6a beta-hexahydro-4β-aminomethyl-2-oxo-2H-cyclopenta[b]furan-5α-carboxylic acid methylester. The free amine was dissolved in 30 ml. of t-butanol and treated at 50° C. with 135 mg. of tertiary butyl hypochlorite dissolved in 5 ml. of tertiary butanol. The mixture was kept at 50° C. for 30 minutes. Evaporation of the organic solvent afforded the N-chloroaminomethyl derivative, i.e., 3,3a beta-4,5,6,6a beta-hexahydro-4β-chloroaminomethyl-2-oxo-2H-cyclopent[b]furan-5α-carboxylic acid methylester. This derivative was suspended in 8 ml. of methanol and treated with a solution of 66 mg. of sodium methoxide in 5 ml. of methanol. The clear solution was then heated under reflux until neutral (2 hours). Cooling and evaporation gave the 3,3a beta-4,5,6,6a beta-hexahydro-4β-iminomethyl-2-oxo-2H-cyclopenta[b]furan-5α-carboxylic acid methyl ester. This compound was then hydrolyzed with 0.1 N aqueous hydrochloric acid to form 3,3a beta-4,5,6,6a beta-hexahydro-4β-carboxaldehyde-2-oxo-2H-cyclopenta[b]furan-5α-carboxylic acid methylester.

EXAMPLE 13

3,3a beta-4,5,6,6a beta-hexahydro-4β-(3-oxo-1-trans-octenyl)-2-oxo-2H-cyclopenta[b]furan-5α-carboxylic acid methylester To a solution of 433 mg. of dimethyl (2-oxoheptyl) phosphonate in 20 ml. of dimethoxy ethylene glycol was added under an argon atmosphere 1.2 ml. of a 1.6 M solution of n-butyl lithium in hexane. After 10 minutes, 400 mg. of 3,3a beta-4,5,6,6a beta-hexahydro-4β-carboxaldehyde-2-oxo-2H-cyclopenta[b]furan-5α-carboxylic acid methylester was added and the mixture stirred for 2 hours. Water was then added (25 ml.) and the mixture extracted with methylene chloride. The methylene chloride solution was dried (MgSO$_4$), treated with activated charcoal and the solvent removed under reduced pressure to give 600 mg. of a brown oil. The product was taken up in a little ethyl acetate, filtered through a small column of silica gel, and the eluate treated with petroleum ether. After 2 days at 0° C. the 3,3a beta-4,5,6,6a beta-hexahydro-4β-(3-oxo-1-trans-octenyl)-2-oxo-2H-cyclopenta[b]furan-5α-carboxylic acid methylester, crystallized as large flat prisms; m.p. 48°-49° C.

EXAMPLE 14

3,3a beta-4,5,6,6a beta-hexahydro-4β-(3α-hydroxy-1-trans-octenyl)-2-oxo-2H-cyclopenta[b]furan-5α-carboxylic acid methylester 5 g. of 3,3a beta-4,5,6,6a beta-hexahydro-4β-(3-oxo-1-transoctenyl)-2-oxo-2H-cyclopenta[b]furan-5α-carboxylic acid methylester was treated with excess zinc borohydride in 50 ml. of dimethoxy ethylene glycol at room temperature (25° C.) for half an hour. After cautious addition of 30 ml. of dilute sulfuric acid, with ice-cooling, the mixture was extracted four times with diethyl ether. Evaporation of the ether gave a mixture from which the pure 3,3a beta-4,5,6,6a beta-hexahydro-4β-(3α-hydroxy-1-trans-octenyl)-2-oxo-2H-cyclopenta[b]furan-5α-carboxylic acid methylester m.p. 58°-61° C. was obtained upon chromatography on silica gel (diethyl ether as eluant). Also obtained by chromatography was the 3,3α beta-4,5,6,6α beta-hexahydro-4β-(3β-hydroxy-1-trans-octenyl)-2-oxo-2H-cyclopenta[b]furan-5α-carboxylic acid methylester which was a colorless oil.

EXAMPLE 15

A mixture of 6.1 g. of 3,3a beta-4,5,6,6a beta-hexahydro-4β-(3α-hydroxy-1-trans-octenyl)-2-oxo-2H-cyclopenta[b]furan-5α-carboxylic acid methylester in 40 ml. of tetrahydrofuran and 9 ml. of 6% by weight aqueous sodium hydroxide was refluxed 3.5 hours. The mixture was cooled with an ice bath and slowly acidified with 2 N-aqueous sulfuric acid. After evaporation of most of the tetrahydrofuran, the residue was saturated with sodium chloride and extracted with ethyl acetate. Evaporation of the ethyl acetate gave 6.0 g. of 2β-(3α-hydroxy-1-trans-octenyl)3α-carboxymethyl-4α-hydroxy-cyclopentane-1α-carboxylic acid.

A benzene solution of the acid was refluxed in a Dean-Stark apparatus until thin layer analysis showed the lactonization was complete. Evaporation of the benzene yielded 3,3a beta-4,5,6,6a beta-hexahydro-4β-(3α-hydroxy-1-trans-octenyl)-2-oxo-2H-cyclopenta[b]furan-5α-carboxylic acid.

EXAMPLE 16

0.1 ml. of acetic anhydride was added at 0° C. to a solution of 0.96 g. of 3,3a beta-4,5,6,6a beta-hexahydro-4β-(3a-hydroxy-1-trans-octenyl)-2-oxo-2H-cyclopenta[b]furan-5α-carboxylic acid in 15 ml. of pyridine. After standing at 25° C. for 15 hours, the reaction mixture was cooled to 0° C. and 3 ml. of water added. After 2 hours, the pyridine was evaporated and the residue dissolved in ethyl acetate. The ethyl acetate solution was washed with 4N-hydrochloric acid then evaporated to yield 1.12 g. of 3,3a beta-4,5,6,6a beta-hexahydro-4β-(3α-acetoxy-1-trans-octenyl)-2-oxo-2H-cyclopenta[b]furan-5α-carboxylic acid, m.p. 34°-36° C. from ethyl ether.

EXAMPLE 17

0.94 g. of 3,3a beta -4,5,6,6a beta-hexahydro-4β-(3α-acetoxy-1-trans-octenyl)-2-oxo-2H-cyclopenta[b]furan-5α-carboxylic acid was reacted with 2 ml. of oxalyl chloride in 10 ml. of benzene at 40° C. for 30 minutes. The excess oxalyl chloride and benzene were evaporated to yield 3,3a beta-4,5,6,6a beta-hexahydro-4β-(3α-acetoxy-1-trans-octenyl)-2-oxo-2H-cyclopenta[b]furan-5α-carboxylic acid chloride. This chloride and 0.48 g. of 97% M-chloroperbenzoic acid were dissolved in 5 ml. of benzene and 0.4 ml. of pyridine was slowly added at 0° C. After 2 hours, 70 ml. of benzene was added and the resulting solution washed successively with 2N-hydrochloric acid, 10% by weight aqueous sodium bicarbonate, and saturated sodium chloride. Evaporation of the benzene at 10°-20° C. yielded 3,3a beta-4,5,6,6a beta-hexahydro-4β-(3α-acetoxy-1-trans-octenyl)-2-oxo-2H-cyclopenta[b]furan-5α-oyl m-chlorobenzoyl peroxide, m.p. 79°-80° C.

EXAMPLE 18

A solution of 0.9 g. of 3,3a beta-4,5,6,6a beta-hexahydro-4β-(3α-acetoxy-1-trans-octenyl)-2-oxo-2H-cyclopenta[b]furan-5α-oyl m-chlorobenzoyl peroxide in 45 ml. of benzene was refluxed for 24 hours. The benzene was evaporated to produce a mixture containing 3,3a beta-4,5,6,6a beta-hexahydro-4 beta-(3 alpha-acetoxy-1-trans-octenyl)-2-oxo-2H-cyclopenta[b]furan-5α-(3-chlorobenzoyloxy) and 3,3a beta-4,5,6,6a beta-hexahydro-4 beta-(3α-acetoxy-1-trans-octenyl)-2-oxo- 2H-cyclopenta[b]furan-5α-(3-chlorobenzoylcarbonyldioxy) as residue. This residue was dissolved in 10 ml. of 23 M lithium methoxide in methanol. After one hour, the reaction was acidified with 4N-hydrochloric acid, saturated with sodium chloride, and extracted with methylene chloride. The combined methylene chloride extracts were washed with 10% by weight aqueous sodium bicarbonate, then evaporated to yield 0.65 g. of material. Chromatography on silica gel afforded 3,3a beta-4,5,6,6a beta-hexahydro-4β-(3α-hydroxy-1-trans-octenyl)-5α-hydroxyl-2-oxo-2H-cyclopenta[b]furan.

EXAMPLE 19

A solution of 2.6 g. of 3,3a beta-4,5,6,6a beta-hexahydro-4β-(3α-hydroxy-1-trans-octenyl)-2-oxo-2H-cyclopenta[b]furan-5α-carboxylic acid methyl ester, 6.9 g. of dihydropyran and 14 mg. of p-toluene-sulfonic acid in 150 ml. of methylene chloride was stirred at 25° C. for 3 hours. The solution was washed with saturated sodium bicarbonate and the volatile components evaporated to give 4 g. of an oil. The oil was dissolved in 1:1 parts by volume ethyl ether-hexane and stored at −17° C. After one day 3,3a beta-4,5,6,6a beta-hexahydro-4β-[3α(2-tetrahydropyranyl-oxy)-1-trans-octenyl]-2-oxo-2H-cyclopenta[b]furan-5α-carboxylic acid methyl ester crystallized as needles; m.p. 64°–65° C.

EXAMPLE 20

A mixture of 1.88 g. of 3,3a beta-4,5,6,6a beta-hexahydro-4β[3α(2-tetrahydropyranyloxy)-1-trans-octenyl]-2-oxo-2H-cyclopenta[b]furan-5α-carboxylic acid methylester, 8.3 ml. of 6% by weight aqueous solution of sodium hydroxide and 33 ml. of tetrahydrofuran was refluxed for 4 hours. The mixture was cooled to 0° C. and neutralized with 2N-aqueous sulfuric acid, saturated with sodium chloride, and extracted with ethyl acetate. Evaporation of the ethyl acetate yielded 2.5 g. of 2β[3α(2-tetrahydropyranyloxy)-1-trans-octenyl]-3α-carboxymethyl-4α-hydroxy-cyclopentane-1α-carboxylic acid; m.p. 114°–115° C.

The acid was mixed with 50 ml. of benzene and the mixture refluxed for 4 hours. Evaporation of the benzene yielded 3,3a beta-4,5,6,6a beta-hexahydro-4β[3α(2-tetrahydropyranyloxy)-1-trans-octenyl]-2-oxo-2H-cyclopenta[b]furan-5α-carboxylic acid; m.p. 73°–74° C. from ethyl ether/hexane.

EXAMPLE 21

A solution of 198 mg. of 3,3a beta-4,5,6,6a beta-hexahydro-4β[3α(2-tetrahydropyranyloxy)-1-trans-octenyl]-2-oxo-2H-cyclopenta[b]furan-5α-carboxylic acid and 88 mg. of 97% m-chloroperbenzoic acid in 7 ml. of ethyl ether/methylene chloride (1:1 parts by volume) was added to an ice cold solution of 110 mg. of dicyclohexylcarbodiimide in 2.5 ml. of ethyl ether. The mixture was kept at −3° C. for 15 hours, then filtered and the filtrate washed successively with saturated ammonium sulfate, 10% sodium bicarbonate; and saturated sodium chloride. Evaporation of the solvent below 25° C. yielded 248 mg. of 3,3a beta-4,5,6,6a beta-hexahydro-4β[3α(2-tetrahydropyranyloxy)-1-trans-octenyl]-2-oxo-2H-cyclopenta[b]furan-5α-oyl m-chloro-benzoyl peroxide.

EXAMPLE 22

The compound of 3,3a beta-4,5,6,6a beta-hexahydro-4β[3α(2-tetrahydropyranyloxy)-1-trans-octenyl]-2H-cyclopenta[b]furan-5α-oyl-m-chlorobenzoyl peroxide was treated in the manner of Example 18 to form 3,3a beta-4,5,6,6a beta-hexahydro-4β[3α(2-tetrahydropyranyl)-1-trans-octenyl]-5α-hydroxy-2-oxo-2H-cyclopenta[b]furan.

This product was then hydrolyzed with 10% aqueous acetic acid in tetrahydrofuran to produce 3,3a beta-4,5,6,6a beta-hexahydro-4β(3α-hydroxy-1-trans-octenyl)-5α-hydroxxy-2-oxo-2H-cyclopenta[b]furan.

EXAMPLE 23

3,3a beta-4,5,6,6a beta-hexahydro-4β-carboxyaldehyde-2-oxo-2H-cyclopenta[b]furan-5α-carboxylic acid methylester oxime To a solution of 1.8 g. of 3,3a beta-4,5,6,6a beta-hexahydro-4β-aminomethyl-2-oxo-2H-cyclopenta[b]furan-5α-carboxylic acid methyl ester in 15 ml. of methanol was added 0.5 g. of sodium tungstate followed by the dropwise addition of 3 ml. of 30–35% aqueous hydrogen peroxide. The temperature was maintained at 15°–20° C. throughout the addition and for 0.5 hours thereafter. The methanol was then removed under reduced pressure and the residue extracted thoroughly with ethyl acetate. The organic layer was dried (MgSO$_4$) and the solvent removed under reduced pressure to give the 3,3a beta-4,5,6,6a beta-hexahydro-4β-carboxaldehyde-2-oxo-2H-cyclopenta[b]furan-5α-carboxylic acid methyl ester oxime.

EXAMPLE 24

3,3a beta-4,5,6,6;1 a beta-hexahydro-4β-carboxyaldehyde-2-oxo-2H-cyclopenta[b]furan-5α-carboxylic acid methyl ester To a solution of 1 g. of 3,3a beta-4,5,6,6a beta-hexahydro-4β-carboxaldehyde-2-oxo-2H-cyclopenta[b]furan-5α-carboxylic acid methyl ester oxime dissolved in 15 ml. of a 50% by volume aqueous ethanolic solution was added 1.5 g. of sodium bisulfite. The resulting mixture was then refluxed for two hours and the ethanol removed under reduced pressure. The residue was then treated with dilute hydrochloric acid and the mixture extracted with chloroform. The organic layer was dried (MgSO$_4$) and the solvent removed under reduced pressure to give 3,3a beta-4,5,6,6a beta-hexahydro-4β-carboxaldehyde-2-oxo-2H-cyclopenta[b]furan-5α-carboxylic acid methyl ester.

EXAMPLE 25

4α-Methoxycarbonyl-3β-cyano-2α-(2-propenyl)cyclopentanone

To a solution of diethylaluminumcyanide (0.2 mole) in 150 ml. of toluene at 0° C. was added a solution of 16 g. of 1-methoxycarbonyl-3-(2-propenyl)-4-oxo-cyclopent-2-ene dissolved in 100 ml. of toluene. After 30 minutes the mixture was poured slowly onto ice-cold 2N-hydrochloric acid and extracted with methylene chloride. The organic extract was dried (MgSO$_4$) and the solvent removed under reduced pressure to give a residue which after distillation afforded the 4α-methoxycarbonyl-3β-cyano-2α-(2-propenyl)cyclopentanone.

EXAMPLE 26

By the procedure of Example 6, 2α-methoxycarbonyl-3β-cyano-2α-(2-propenyl)-cyclopentanone was converted to 2α-carboxymethyl-3β-cyano-4α-methoxycarbonyl-cyclopentanone.

EXAMPLE 27

3,3a beta-4,5,6,6a beta-hexahydro-4β-cyano-2-oxo-2H-cyclopenta[b]furan-5α-carboxylic acid methylester To an ice-cold solution of 4.66 g. of 2α-carboxymethyl-3β-cyano-4α-methoxycarbonylcyclopentanone in 250 ml. of methanol was added 0.94 g. of sodium methoxide followed by the addition of 0.5 g. of sodium borohydride. The mixture was stirred at 0° C. for one hour and then acidified with 1N-aqueous sulfuric acid. Evaporation of the methanol left 2α-carboxymethyl-3β-cyano-4α-methoxycarbonylcyclopentanol as a liquid residue which was extracted with a 20% by volume acetone in 80% ethyl acetate solution. The solution was dried and the solvent removed under reduced pressure. The residue was then dissolved in tetrahydrofuran and refluxed for 2 hours. The solvent was then removed and the residue treated with 15 ml. of water containing 2 g. of potassium bicarbonate. The solid was filtered to give 3,3a beta-4,5,6,6a beta-hexahydro-4β-cyano-2-oxo-2H-cyclopenta[b]furan-5α-carboxylic acid methylester.

EXAMPLE 28

3,3a beta-4,5,6,6a beta-hexahydro-4β-aminomethyl-2-oxo-2H-cyclopenta[b]furan-5α-carboxylic acid methylester hydrochloride 635 mg. of 3,3a beta-4,5,6,6a beta-hexahydro-4β-cyano-2-oxo-2H-cyclopenta[b]furan-5α-carboxylic acid methylester was dissolved in 100 ml. of ethanol and hydrogenated in the presence of 190 mg. of platinum oxide at room temperature in a Parrhydrogenator (53 p.s.i.) for 3½ hours. The catalyst was filtered off, the filtrate evaporated, and the free amine residue treated with ethanolic hydrogen chloride. The ethanol was removed under reduced pressure and the remaining solid suspended in an ethanol ethyl-acetate mixture giving 605 mg. of 3,3a beta-4,5,6,6a beta-hexahydro-4β-aminomethyl-2-oxo-2H-cyclopenta[b]furan-5α-carboxylic acid methylester hydrochloride.

EXAMPLE 29

2-Allyl-1,3-cyclohexanedione

Allyl bromide (195 g., 1.62 mol.) was added over a 15 minute period to a stirred ice-cold mixture of cyclohexanedione (165 g., 1.47 mol.), copper-bronze (4.5 g.), and 330 ml. of 20% by weight aqueous potassium hydroxide. After 6 hours, the reaction was mixed with 1500 ml. of a 5% by weight aqueous sodium hydroxide solution and 1000 ml. of ethyl ether, filtered and the separated water layer acidified with 4N aqueous hydrochloric acid to pH 1. A brown solid (188 g.) formed upon refrigeration at 0° C. The solid was taken up in ethyl acetate and the solution was washed with water (3×150 ml.), dried (MgSO₄), treated with charcoal, and condensed until turbid. Upon cooling, 126 g. (57%) of 2-allyl-1,3-cyclohexanedione was collected, m.p. 125°–127° C.

EXAMPLE 30

By the procedure of Example 29, allyl bromide is reacted with 5-methyl-1,3-cyclohexanedione to produce 2-allyl-5-methyl-1,3-cyclohexanedione.

EXAMPLE 31

2-Chloro-2-allyl-1,3-cyclohexanedione t-Butylhypochlorite (104.6 g, 0196 mol) was added dropwise to a solution of 2-allyl-1,3-cyclohexanedione (132 g, 0.87 mol) in 650 ml of methanol at 0° C. The temperature was not allowed to rise above 20° C. The methanol was removed at reduced pressure in a 40° water bath and the residual oil was taken up in benzene. The benzene solution was washed with 5 percent sodium thiosulfate (3×250 ml), 5 percent sodium bicarbonate (3×250 ml) and water (1×250 ml). Evaporation of the benzene gave 148 g (91 percent) of 2-chloro-2-allyl-1,3-cyclohexanedione as a light yellow oil.

EXAMPLE 32

By the procedure of Example 31 2-allyl-5-methyl-1,3-cyclo-hexanedione was converted to 2-chloro-2-allyl-5-methyl-1,3-cyclohexanedione.

EXAMPLE 33

2-Allyl-2-cyclopenten-1-one

Anhydrous powdered sodium carbonate (670 g) and 1300 ml of dry (alumina) xylene were placed in a 3-l., three-necked flask equipped with a Dean-Stark trap, condenser, vibra-mixer, dropping funnel and argon inlet. The flask was flushed with argon and the contents brought to reflux. A solution of 2-chloro-2-allyl-1, 3-cyclohexanedione (147 g, 0.79 mol) in 200 ml of xylene was added dropwise at such a rate that strong refluxing was maintained. After 4.5 hr, the reaction was cooled, filtered, and the sodium carbonate cake washed thoroughly with ethyl acetate. Evaporation of the solvent and careful fractionization of the residual oil gave 47.8 g (50 percent) of 2-allyl-2-cyclopenten-1-one, bp 73°–84°/4.2 mm.

EXAMPLE 34

By the procedure of Example 33 2-chloro-2-allyl-5-methyl-1,3-cyclohexanedione was converted to 2-allyl-4-methyl-2-cyclopenten-1-one.

EXAMPLE 35

2-alpha-Allyl-3-beta-nitromethylcyclopentaneone

A solution of 2-allyl-2-cyclopenten-1-one (46.8 g, 0.38 mol), 180 ml of nitromethane and 12 ml of Triton B[1] (35 percent by weight in methanol) was heated for 4 hr in an oil bath at 60°–65° C. The reaction mixture was cooled, acidified to pH 1 with 1N aqueous sulfuric acid, diluted with 500 ml of ethyl ether, washed with saturated aqueous sodium chloride solution (2×250 ml), and dried (MgSO₄). Evaporation of the solvent gave 69 g (100 percent) of 2-alpha-allyl-3 beta-nitromethylcyclopentaneone as a yellow oil. The compound can be further purified by distillation, bp 110°–112°/0.025 mmHg.

[1] benzyltrimethyl ammonium hydroxide

EXAMPLE 36

By the procedure of Example 35 2-allyl-4-methyl-2-cyclopenten-1-one was converted to 2-alpha-allyl-3 beta-nitromethyl-4alpha-methylcyclopentan-1-one.

EXAMPLE 37

2-alpha-Carboxymethyl-3 beta-nitromethylcyclopentan-1-one

A solution of sodium permanganate (52.2 g, 0.26 mol) in 140 ml of water was added dropwise over a 1 hr period to a rapidly stirred mixture of 2-alpha-allyl-3 beta-nitromethylcyclopentaneone (18.3 g, 0.1 mol), 300 ml of acetone, and 83 ml of 10 percent (v/v) sulfuric acid under argon at $-10°-0°$. The reaction was stirred an additional 45 min at 0° C., then saturated with sodium chloride and extracted with 3:7 tetrahydrofuran-methylene chloride. The combined organic extracts were dried (MgSO$_4$) and evaporated to give 23.2 g of crude 2 alpha-carboxymethyl-3 beta-nitromethylcyclopentan-1-one as an oil which crystallized from ethyl acetate-ethyl ether (1:4); mp 88°–90° C.

EXAMPLE 38

By the procedure of Example 37, 2 alpha-allyl-3 beta-nitromethyl-4 alpha-methylcyclopentan-1-one was converted to 2 alpha-carboxymethyl-3 beta-nitromethyl-4 alpha-methyl cyclopentan-1-one.

EXAMPLE 39

3,3a beta-4,5,6,6a beta-Hexahydro-4 beta-nitromethyl-2-oxo-2H-cyclopenta[b]furan A solution of compound 2 alpha-carboxymethyl-3 beta-nitromethylcyclopentan-1-one (2.01 g, 10 mmol) in 20 ml of tetrahydrofuran was treated dropwise under argon at $-78°$ C. with 20 ml (21.6 mmol) of a 1.06 M tetrahydrofuran solution of lithium perhydro-9b-boraphenalylhydride. The reaction was stirred for 30 min then allowed to warm to 0° C. At this point it was poured into a separatory funnel containing 200 ml of cyclohexane, 150 ml of ethyl acetate, and 50 ml of water. The water layer was separated and the organic phase washed with water (2×20 ml). The combined water extracts were immediately acidified to pH 1 with 4N aqueous hydrochloric acid, saturated with sodium chloride and extracted with 3:7 parts by volume tetrahydrofuran-methylene chloride (3×50 ml) solution. The combined organic extracts were dried (MgSO$_4$) and condensed to give 2.1 g of a colorless oil which was taken up in 200 ml of benzene and refluxed for 2 hr in a Dean-Stark apparatus. The resulting benzene solution was washed with 5 percent by weight aqueous sodium bicarbonate (2×10 ml), dried (MgSO$_4$), and condensed to give 1.15 g (62 percent) of 3,3a beta-4,5,6,6a beta-hexahydro-4 beta-nitromethyl-2-oxo-2H-cyclopenta[b]furan as a colorless oil.

EXAMPLE 40

By the procedure of Example 39, 2 alpha-carboxymethyl-3 beta-nitromethyl-4 alpha-methyl cyclopentan-1-one is converted to 3,3a beta-4,5,6,6a beta-hexahydro-4-beta-nitromethyl-5, alpha-methyl-2-oxo-2H-cyclopenta[b]furan.

EXAMPLE 41

3,3a beta-4,5,6,6a beta-Hexahydro-4-beta-nitromethyl-2-oxo-2H-cyclopenta[b]furan and

2 alpha-Carboxymethyl-3 beta-nitromethyl-1-cyclopentane-1 beta-ol

To an ice cold solution of 3.8 g of 2 alpha-carboxymethyl-3 beta-nitromethylcyclopentan-1-one in 200 ml of methanol was added 1.08 g of sodium methoxide followed by 0.6 g of sodium borohydride. The mixture was stirred at 0° C. for 1 hr and then acidified with 1N aqueous sulfuric acid. Evaporation of the methanol left 2 alpha-carboxymethyl-3 beta-nitromethyl-4 alpha-methylcyclopentanol as a liquid residue which was extracted with a 20 percent by volume acetone in ethylacetate solution. The solution was dried and the solvent removed under reduced pressure. The residue was then dissolved in tetrahydrofuran and refluxed 2 hr. The solvent was then removed and the residue treated with 15 ml of water containing 2 g of potassium bicarbonate. The mixture was extracted with methylene chloride and the organic layer dried (MgSO$_4$). The solvent was then removed under reduced pressure to give the 3,3a beta-4,5,6,6a beta-hexahydro-4 beta-nitromethyl-2-oxo-2H-cyclopenta[b]furan.

The bicarbonate solution was acidified and extracted with 2:1 parts by volume of a solution of methylene-chloride-acetone. The organic solution was dried (MgSO$_4$) and the solvent removed under reduced pressure to give 2 alpha-carboxymethyl-3 beta-nitromethyl-1-cyclopentane-1 beta-ol, mp 84°–85° C.

EXAMPLE 42

By the procedure of Example 41 2 alpha-carboxymethyl-3 beta-nitromethyl-4 alpha-methyl cyclopentan-1-one is converted into the isomers 3,3a beta-4,5,6,6a beta-hexahydro-4 beta nitromethyl-5 alpha-methyl-2-oxo-2H-cyclopenta[b]furan and 2 alpha-carboxymethyl-3 beta-nitromethyl-5 alpha-methyl-1-cyclopentan-1 beta-ol.

EXAMPLE 43

3,3a beta-4,5,6,6a beta-Hexahydro-4 beta-formyl-2-oxo-2H-cyclopenta[b]furan

A solution of 3,3a beta-4,5,6,6a beta-hexahydro-4 beta-nitromethyl-2-oxo-2H-cyclopenta[b]furan (1.08 g, 4.85 mmol) in 35 ml of absolute methanol was treated at 0° C. under argon with 2.6 ml (6.0 mmol) of a 2.3 M lithium methoxide in methanol solution. The solvent was evaporated and the residual solid dried at 25° C. in vacuo. To the dry salt under argon at $-10°-0°$ C. was added 15 ml of saturated borax solution followed by the dropwise addition of sodium permanganate trihydrate (0.69 g, 3.5 mmol) in 6 ml of water. The reaction mixture was immediately filtered through celite and extracted with 8:2 methylene chloride-acetone (4×60 ml). Evaporation of the dried (MgSO$_4$) organic extracts gave 0.50 g (55 percent of 3,3a beta-4,5,6,6a beta-hexahydro-4 beta-formyl-2-oxo-2H-cyclopenta[b]furan as an oil.

EXAMPLE 44

By the procedure of Example 43, 3,3a beta-4,5,6,6a beta-hexahydro-4 beta nitromethyl-5 alpha-methyl-2oxo-2H-cyclopenta[b]furan was converted to 3,3a beta-4,5,6,6a beta-hexahydro-4 beta-formyl-5 alpha methyl-2-oxo-2H-cyclopenta[b]furan.

EXAMPLE 45

3,3a beta-4,5,6,6a beta-hexahydro-4 beta-(3-oxo-1-trans-octenyl)-5 alpha-methyl-2-oxo-2H-cyclopenta[b]furan To a suspension of 0.72 g. of sodium hydride in 150 ml. of dry glyme was added 6 g. of dimethyl(2-oxoheptyl) phosphonate. After stirring for 1.5 hour, 5 g. of 3,3a beta-4,5,6,6a beta-hexahydro-4 beta-formyl-5 alpha-methyl-2-oxo-2H-cyclopenta[b]furan dissolved in 30 ml. of glyme was added dropwise at 0° C. After stirring for 3 hours at room temperature, 500 ml. of diethyl ether was added and the mixture washed with water. The organic layer was then dried (MgSO$_4$) and the solvent removed under reduced pressure. The residue was then washed through 75 g. of silica gel to give 7.1 g. of 3,3a beta-4,5,6,6a beta-hexahydro-4 beta-(5-oxo-1-trans-octenyl)-5 alpha-methyl-2-oxo-2H-cyclopenta[b]furan.

EXAMPLE 46

By the procedure of Example 45, 3,3a beta-4,5,6,6a beta-hexahydro-4 beta-formyl-2-oxo-2H-cyclopenta[b]furan was converted to 3,3a beta-4,5,6,6a beta-hexahydro-4 beta-(5-oxo-1-trans-octenyl)-2-oxo-2H-cyclopenta[b]furan.

EXAMPLE 47

3,3a beta-4,5,6,6a beta-Hexahydro-4 beta(3 alpha-hydroxy-1-trans-octenyl)-5 alpha-methyl-2-oxo-2H-cyclopenta[b]furan To a solution of 4.5 g of 3,3a beta-4,5,6,6a beta-hexahydro-4 beta-(3-oxo-1-trans-octenyl)-5 alpha-methyl-2-oxo-2H-cyclopenta[b]furan in 100 ml of dry glyme was added an excess of zinc borohydride in 50 ml of glyme and the resulting solution stirred for 3 hr. The solution was cooled to 0° centigrade and treated with 200 ml of water, 400 ml of ether and 10 ml of 0.5 N aqueous sulfuric acid. The ether was separated and dried (MgSO$_4$) and the solvent removed under reduced pressure to give 3,3a beta-4,5,6,6a beta-hexahydro-4 beta-(3-hydroxy-1-trans-octenyl)-5 alpha-methyl-2-oxo-2H-cyclopenta[b]furan. Chromatography on silica gel then afforded the 3,3a beta-4,5,6,6a beta-hexahydro-4 beta-(3 alpha-hydroxy-1-trans-octenyl)5 beta-methyl-2-oxo-2H-cyclopenta[b]furan. Also obtained by chromatography was the 3,3a beta-4,5,6,6a beta-hexahydro-4 beta(3 beta-hydroxy-1-trans-octenyl)-5 beta-methyl-2-oxo-2H-cyclopenta[b]furan.

EXAMPLE 48

By the procedure of Example 47, 3,3a beta-4,5,6,6a beta-hexahydro-4 beta-(3-oxo-1-trans-octenyl)-2-oxo-2H-cyclopenta[b]furan was converted to 3,3a beta-4,5,6,6a beta-hexahydro-4 beta (3 beta-hydroxy-1-trans-octenyl)-2-oxo-2H-cyclopenta[b]furan.

EXAMPLE 49

3,3a beta-4,5,6,6a beta-Hexahydro-4-beta-[3 alpha(2-tetrahydropyranyloxy)-1-trans-octenyl]-5 alpha-methyl-2-oxo-2H-cyclopenta[b]furan A solution of 5 g of 3,3a beta-4,5,6,6a beta-hexahydro-4 beta-(3 alpha-hydroxy-1-trans-octenyl)-5 alpha-methyl-2-oxo-2H-cyclopenta[b]furan, 12 g of dihydropyran and 25 mg of p-toluene sulfonic acid in 200 ml of methylene chloride was stirred at 25° C. for 3 hr. The solution was washed with saturated sodium bicarbonate solution, the methylene chloride solution dried (MgSO$_4$) and the volatile components evaporated under reduced pressure to give 6.4 g of 3,3a beta-4,5,6,6a beta-hexahydro-4 beta[3 alpha(2-tetrahydropyranyloxy)-1-trans-octenyl]5 alpha-methyl-2-oxo-2H-cyclopenta[b]furan.

EXAMPLE 50

By the procedure of Example 49, 3,3a beta-4,5,6,6a beta-hexa-hydro 4 beta-(3 beta-hydroxy-1-trans-octenyl)-2-oxo-2H cyclopenta[b]furan was converted to 3,3a beta-4,5,6,6a beta-hexahydro-4 beta [3-alpha-(2-tetrahydropyranyloxy)-1-trans-octenyl]-2-oxo-2H-cyclopenta[b]furan.

EXAMPLE 51

3,3a beta-4,5,6,6a beta-Hexahydro-4 beta[3 alpha(2-tetrahydropyranyloxy)-1-trans-octenyl]5 alpha-methyl-2-hydroxy-2H-cyclopenta[b]furan To a solution of 5.3 g of 3,3a beta-4,5,6,6a beta-hexahydro-4 beta-[3 alpha(2 tetrahydropyranyloxy)-1-trans-octenyl]5 alpha-methyl-2-oxo-2H-cyclopenta[b]furan in 150 ml of toluene, was added dropwise at −73° C., 2 equivalents of diisobutylaluminum hydride in the same solvent. The reaction mixture was stirred at this temperature for 2 hr after which time 20 ml of methanol was slowly added and the mixture stirred for 2 hr at room temperature. The mixture was then filtered thru a bed of charcoal, the charcoal was washed with ethyl acetate and the solvents were then removed under reduced pressure. The residue was then washed thru a column of silica gel to give 3,3a beta-4,5,6,6a beta-hexahydro-4 beta [3 alpha(2-tetrahydropyranyloxy)1-trans-octenyl]5 alpha-methyl-2-hydroxy-2H-cyclopenta[b]furan.

EXAMPLE 52

By the procedure of Example 51, 3,3a beta-4,5,6,6a beta hexahydro-4 beta-[3 alpha(2-tetrahydropyranyloxy)-1-trans-octenyl]-2-oxo-2H-cyclopenta[b]furan was converted to 3,3a beta-4,5,6,6a beta-hexahydro-4 beta[3 alpha(2-tetrahydropyranyloxy)-1-trans-octenyl]-2-hydroxy-2H-cyclopenta[b]furan.

EXAMPLE 53

7-[[3 alpha-methyl-5 alpha-hydroxy-2 beta[3 alpha(2-tetrahydropyranyloxy)-1-trans-octenyl]cyclopentyl]]-cis-5-heptenoic acid A solution of 200 mg of 3,3a beta-4,5,6,6a beta-hexahydro-4 beta[3 alpha(2-tetrahydropyranyloxy)-1-trans-octenyl]5 alpha-methyl-2-hydroxy-2H-cyclopenta[b]furan in 3 ml of dimethylsulfoxide was added to 10 ml of a solution of 2.8 equivalents of the Wittig reagent prepared from 4-carboxybutyltriphenylphosphonium bromide and dimsylsodium. After 3 hr at 25° C. the mixture was poured into 30 ml of dilute brine and acidified to pH 3 with phosphoric acid. The mixture was extracted with pentane and the product separated by column chromatography to give 7[[3 alpha-methyl-5 alpha-hydroxy-2 beta[3alpha-(2tetrahydropyranyloxy)-1-transoctenyl]cyclopentyl]]-cis-5-heptenoic acid.

EXAMPLE 54

By the procedure of Example 53, 3,3a beta-4,5,6,6a beta-hexahydro-4 beta[3 alpha(2-tetrahydropyranyloxy)-1-transoctenyl]-2 hydroxy-2H-cyclopenta[b]furan is converted to 7[[5-alpha-hydroxy-2 beta [3 alpha-(2-tetrahydropyranyloxy)-1-trans octenyl] cyclopentyl]]-cis-5-heptenoic acid.

EXAMPLE 55

7[3 alpha-Methyl-5-oxo-2 beta (3 alpha-hydroxy-1-trans-octenyl)cyclopentyl]cis-5-heptenoic acid To a mixture of 6 g of chromium trioxide and 9.5 g of pyridine in 150 ml of methylene chloride was added at 0° C. 4.5 g of [[3 alpha-methyl-5 alpha-hydroxy-2 beta[3 alpha-(2-tetrahydropyranyloxy)-1-trans-octenyl]cyclopentyl]]cis-5-heptenoic acid dissolved in 50 ml of methylene chloride. The mixture was stirred for 1 hr at room temperature and the mixture filtered thru a bed of celite. The celite was washed with methylene chloride and the combined methylene chloride solution washed with dilute hydrochloric acid to remove any remaining pyridine. The methylene chloride was then removed under reduced pressure and the residue treated with 50 ml of 3:1 parts by volume acetic acid/water solution at 35° C. for 15 hr. The solvents were then removed under high vacuum and the residue purified by column chromatography to give 7-[3 alpha-methyl-5-oxo-2 beta(3 alpha-hydroxy-1trans-octenyl)cyclopentyl]cis-5-heptenoic acid.

EXAMPLE 56

By the procedure of Example 55, 7[[5-alpha-hydroxy-2 beta [3 alpha-(2-tetrahydropyranyloxy)-1-trans-octenyl]cyclopentyl]]cis-5-heptenoic acid was converted to 7[5-oxo-2 beta(3 alpha-hydroxy-1-trans-octenyl)cyclopenyl]cis-5-heptenoic acid.

EXAMPLE 57

7[3 alpha-Methyl-5 alpha-hydroxy-2 beta(3 alpha-hydroxy-1-transoctenyl)cyclopentyl]cis-5-heptenoic acid A solution of 200 mg of 7-[[3 alpha-methyl-5 alpha-hydroxy-2 beta[3 alpha-(2-tetrapyranyloxy)-1-trans-octenyl]cyclopentyl]]-cis-5-heptenoic acid in 5 ml of a 3:1 parts by volume acetic acid/water solution was kept at 35° C. for 15 hr. The solvent was then removed under high vacuum and the residue purified via column chromatography to give 7[3 alpha-methyl-5 alpha-hydroxy-2 beta(3 alpha-hydroxy-1-trans-octenyl)cyclopentyl]cis-5-heptenoic acid.

EXAMPLE 58

By the procedure of Example 57, 7[[5 alpha-hydroxy-2 beta [3 alpha-(2-tetrahydropyranyloxy)-1-trans-octenyl]cyclopentyl]]-cis-5-heptenoic acid was converted 7[3 alpha-hydroxy-2 beta (3 alpha-hydroxy-1-trans-octenyl)cyclopentyl]cis-5-heptenoic acid.

We claim:

1. A compound of the formula

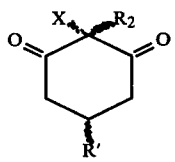

wherein X is hydrogen, bromine or chlorine; R' is hydrogen, lower alkyl or —COOR$_4$; R$_4$ is lower alkyl, benzyl or phenyl; R$_2$ is

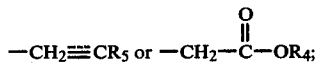

and R$_5$ is hydrogen or lower alkyl; and the dotted bond can be optionally hydrogenated.

2. The compound of claim 1 wherein said compound is methyl-4-chloro-4-(2-propenyl)-3,5-cyclohexanedione carboxylate.

* * * * *